US010259847B2

(12) United States Patent
Obrecht et al.

(10) Patent No.: US 10,259,847 B2
(45) Date of Patent: *Apr. 16, 2019

(54) BETA-HAIRPIN PEPTIDOMIMETICS

(71) Applicant: POLYPHOR AG, Allschwil (CH)

(72) Inventors: Daniel Obrecht, Bättwil (CH); Anatol Luther, Binzen (DE); Francesca Bernardini, Hésingue (FR); Gildas Deniau, Zürich (CH); Alexander Lederer, Basel (CH)

(73) Assignee: Polyphor AG, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/515,445

(22) PCT Filed: Sep. 29, 2015

(86) PCT No.: PCT/EP2015/025067
§ 371 (c)(1),
(2) Date: Mar. 29, 2017

(87) PCT Pub. No.: WO2016/050360
PCT Pub. Date: Apr. 7, 2016

(65) Prior Publication Data
US 2017/0253634 A1    Sep. 7, 2017

(30) Foreign Application Priority Data

Sep. 30, 2014   (EP) ..................... 14003373

(51) Int. Cl.
*C07K 7/64*    (2006.01)
*A61K 38/00*   (2006.01)

(52) U.S. Cl.
CPC .............. *C07K 7/64* (2013.01); *A61K 38/00* (2013.01); *Y02A 50/473* (2018.01)

(58) Field of Classification Search
None
See application file for complete search history.

(56) References Cited

FOREIGN PATENT DOCUMENTS

| WO | WO 2007/079597 A1 | 7/2007 |
| WO | WO 2012/016595 A1 | 2/2012 |
| WO | WO 2013/050346 A1 | 4/2013 |
| WO | WO 2014/161781 A1 | 10/2014 |
| WO | WO 2014/161782 A1 | 10/2014 |

OTHER PUBLICATIONS

International Search Report for PCT/EP2015/025067 dated Feb. 10, 2016.
Written Opinion of the International Searching Authority for PCT/EP2015/025067 dated Feb. 10, 2016.

*Primary Examiner* — Thomas S Heard
(74) *Attorney, Agent, or Firm* — Birch, Stewart, Kolasch & Birch, LLP

(57) ABSTRACT

Beta-hairpin peptidomimetics of the general formula (I), cyclo[$P^1$-$P^2$-$P^3$-$P^4$-$P^5$-$P^6$-$P^7$-$P^8$-$P^9$-$P^{10}$-$P^{11}$-$P^{12}$-$T^1$-$T^2$], and pharmaceutically acceptable salts thereof, with $P^1$ to $P^{12}$, $T^1$ and $T^2$ being elements as defined in the description and the claims, have Gram-negative antimicrobial activity to e.g. inhibit the growth or to kill microorganisms such as *Klebsiella pneumoniae* and/or *Acinetobacter baumannii* and/or *Escherichia coli*. They can be used as medicaments to treat or prevent infections or as disinfectants for foodstuffs, cosmetics, medicaments or other nutrient-containing materials. These peptidomimetics can be manufactured by a process which is based on a mixed solid- and solution phase synthetic strategy.

11 Claims, No Drawings

BETA-HAIRPIN PEPTIDOMIMETICS

The present invention provides β-hairpin peptidomimetics having Gram-negative antimicrobial activity and being embraced by the general disclosures of, but not specifically disclosed in, WO02/070547 A1 and WO2004/018503 A1.

The β-hairpin peptidomimetics of the invention are compounds of the general formula (I), cyclo[$P^1$-$P^2$-$P^3$-$P^4$-$P^5$-$P^6$-$P^7$-$P^8$-$P^9$-$P^{10}$-$P^{11}$-$P^{12}$-$T^1$-$T^2$], and pharmaceutically acceptable salts thereof, with $P^1$ to $P^{12}$, $T^1$ and $T^2$ being elements as described herein below.

In addition, the present invention provides an efficient synthetic process by which these compounds can, if desired, be made in parallel library-format. Moreover, the β-hairpin peptidomimetics of the invention show improved efficacy, reduced hemolysis of red blood cells and reduced or no cytotoxicity.

A major cause of death worldwide and a leading cause of mortality in developed countries are infectious diseases. They result from the presence of pathogenic microbial agents including pathogenic viruses and pathogenic bacteria. The problem of bacterial resistance to established antibiotics has stimulated intense interest in developing novel antimicrobial agents with new modes of action (D. Obrecht, J. A. Robinson, F. Bernadini, C. Bisang, S. J. DeMarco, K. Moehle, F. O. Gombert, *Curr. Med. Chem.* 2009, 16, 42-65; H. Breithaupt, *Nat. Biotechnol.* 1999, 17, 1165-1169).

A growing unmet medical need is represented by Gram-negative bacteria causing 60% of nosocomial pneumonias (R. Frechette, *Ann. Rep. Med. Chem., Elsevier,* 2007, 349-64). Extended spectrum beta lactamase (ESBL)-producing Gram-negative bacteria have also compromised the utility of many front-line beta-lactam drugs (S. J. Projan, P. A. Bradford, *Curr. Opin. Microbiol.,* 2007, 10, 441). The lack of suitable new compounds is forcing clinicians to use previously discarded antibiotics like colistin, despite well-known toxicity problems (M. E. Falagas, S. K. Kasiakou, *Crit. Care,* 2006, 10, R 27).

Therefore, novel approaches are needed to treat inter alia resistant strains of *Klebsiella pneumoniae, Acinetobacter baumannii* and *Escherichia coli* (H. W. Boucher, G. H. Talbot, J. S. Bradley, J. E. Edwards Jr, D. Gilbert, L. B. Rice, M. Scheld, B. Spellberg, J. Bartlett, IDSA Report on Development Pipeline, CID 2009, 48, 1).

One emerging class of antibiotics is based on naturally occurring cationic peptides (T. Ganz, R. I. Lehrer, *Mol. Medicine Today* 1999, 5, 292-297; R. M. Epand, H. J. Vogel, *Biochim. Biophys. Acta* 1999, 1462, 11-28). These include disulfide-bridged β-hairpin and β-sheet peptides (such as the protegrins [V. N. Kokryakov, S. S. L. Harwig, E. A. Panyutich, A. A. Shevchenko, G. M. Aleshina, O. V. Shamova, H. A. Korneva, R. I. Lehrer, *FEBS Lett.* 1993, 327, 231-236], tachyplesins [T. Nakamura, H. Furunaka, T. Miyata, F. Tokunaga, T. Muta, S. Iwanaga, M. Niwa, T. Takao, Y. Shimonishi, *J. Biol. Chem.* 1988, 263, 16709-16713], and the defensins [R. I. Lehrer, A. K. Lichtenstein, T. Ganz, *Annu. Rev. Immunol.* 1993, 11, 105-128], amphipathic α-helical peptides (e.g. cecropins, dermaseptins, magainins, and mellitins [A. Tossi, L. Sandri, A. Giangaspero, *Biopolymers* 2000, 55, 4-30]), as well as other linear and loop-structured peptides. Although the mechanisms of action of antimicrobial cationic peptides are not yet fully understood, their primary site of interaction is the microbial cell membrane (H. W. Huang, *Biochemistry* 2000, 39, 8347-8352). Upon exposure to these agents, the cell membrane undergoes permeabilization, which is followed by rapid cell death. However, more complex mechanisms of action, for example, involving receptor-mediated signaling, cannot presently be ruled out (M. Wu, E. Maier, R. Benz, R. E. Hancock, *Biochemistry* 1999, 38, 7235-7242).

In the compounds described below, a strategy is introduced to stabilize 1-hairpin conformations in backbone-cyclic cationic peptide mimetics exhibiting Gram-negative antimicrobial activity, in particular against Gram-negative pathogens of the so-called ESKAPE pathogens (L. B. Rice, *J. Infect. Dis.* 2008, 197, 1079). This involves transplanting the hairpin sequence onto a template, whose function is to restrain the peptide loop backbone into hairpin geometry. The introduction of additional β-strand linkages may further enhance the rigidity of the hairpin.

Template-bound hairpin mimetic peptides have been described in the literature (D. Obrecht, M. Altorfer, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). Antibacterial template-fixed peptidomimetics and methods for their synthesis have been described in international patent applications WO02/070547 A1, WO2004/018503 A1, WO2007/079605 A2 and WO2012/016595 A1 but these molecules do not show Gram-negative antimicrobial activity having high potency against *Klebsiella pneumoniae* and/or *Acinetobacter baumannii* and/or *Escherichia coli.*

The present invention relates to novel β-hairpin peptidomimetics of formula (I),

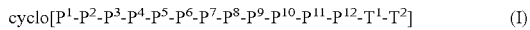

cyclo[$P^1$-$P^2$-$P^3$-$P^4$-$P^5$-$P^6$-$P^7$-$P^8$-$P^9$-$P^{10}$-$P^{11}$-$P^{12}$-$T^1$-$T^2$]    (I)

wherein the single elements T or P are connected in either direction from the carbonyl (C=O) point of attachment to the nitrogen (N) of the next element and wherein $T^1$ is a naturally or non-naturally occurring D α-amino acid containing an optionally substituted side-chain which forms a four- or five-membered heterocycle or a bicyclic system comprising the α-carbon and the α-amino atom;

$T^2$ is a naturally or non-naturally occurring L α-amino acid containing an optionally substituted side-chain which forms a five- or six-membered heterocycle or a bicyclic system comprising the α-carbon and the α-amino atom; or a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function;

$P^1$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or a naturally or non-naturally occurring L α-amino acid containing in total 1 to 25 carbon- and/or heteroatoms in a single side-chain comprising at least one urea function, amide function, ester function, sulfone function or ether function; or a naturally or non-naturally occurring alcoholic L α-amino acid containing in total 1 to 25 carbon- and/or heteroatoms in a single side-chain;

$P^2$ is a naturally or non-naturally occurring aromatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function;

$P^3$, $P^8$ and $P^{10}$ are independently
a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain;

$P^4$ is a naturally or non-naturally occurring aliphatic L α-amino acid containing in total 1 to 25 carbon- and/or heteroatoms in a single side-chain; or a naturally or non-naturally occurring basic L α-amino acid containing in total 1 to 25 carbon- and/or heteroatoms in a single side-chain comprising at least one amino function; or a naturally or non-naturally occurring L α-amino acid containing in total 1 to 25 carbon- and/or heteroatoms in a single side-chain comprising at least one urea function, amide function, ester function, sulfone function or ether function; or a naturally or non-naturally occurring alcoholic L α-amino acid containing in total 1 to 25 carbon- and/or heteroatoms in a single side-chain;

$P^5$ is a naturally or non-naturally occurring basic L α-amino acid containing in total 1 to 25 carbon- and/or heteroatoms in a single side-chain comprising at least one amino function; or a naturally or non-naturally occurring L α-amino acid containing in total 1 to 25 carbon- and/or heteroatoms in a single side-chain comprising at least one urea function, amide function, ester function, sulfone function or ether function; or a naturally or non-naturally occurring alcoholic L α-amino acid containing in total 1 to 25 carbon- and/or heteroatoms in a single side-chain;

$P^6$ is Gly; or a naturally or non-naturally occurring basic D or L α-amino acid containing in total 1 to 25 carbon- and/or heteroatoms in a single side-chain comprising at least one amino function;

$P^7$ is a naturally or non-naturally occurring basic L α-amino acid containing in total 1 to 25 carbon- and/or heteroatoms in a single side-chain comprising at least one amino function;

$P^9$, $P^{11}$ and $P^{12}$ are independently
a naturally or non-naturally occurring L α-amino acid containing in total 1 to 25 carbon- and/or heteroatoms in a single side-chain;

$P^2$ and $P^{11}$ taken together and/or $P^4$ and $P^9$ taken together can form naturally or non-naturally cross-linking D or L α-amino acids containing each in total 1 to 12 carbon- and/or heteroatoms in a single side-chain which together are connecting $P^2$ and $P^{11}$ and/or $P^4$ and $P^9$ by covalent interaction (interstrand linkage);

or a tautomer or rotamer thereof, or a salt, or a hydrate or solvate thereof;

and with the proviso that
if no interstrand linkage is formed;
and
$T^1$ is a naturally or non-naturally occurring D α-amino acid containing an optionally substituted side-chain which forms a five-membered heterocycle or a bicyclic system comprising the α-carbon and the α-amino atom;
then
$T^2$ is a naturally or non-naturally occurring aliphatic L α-amino acid containing in total 1 to 25 carbon- and/or heteroatoms in a single side-chain; or a naturally or non-naturally occurring aromatic L α-amino acid containing in total 1 to 25 carbon- and/or heteroatoms in a single side-chain; or an L α-amino acid of formula $AA10^a$.

A particular embodiment of the present invention relates to compounds according to general formula (I), wherein $T^1$ is an D α-amino acid residue of one of the formulae

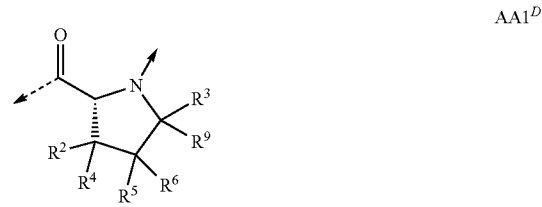

AA1$^D$

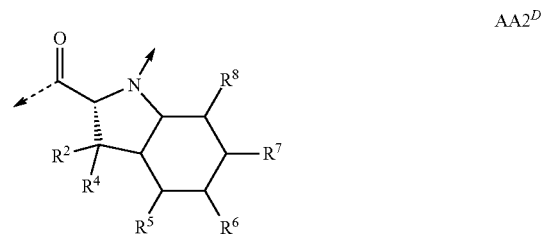

AA2$^D$

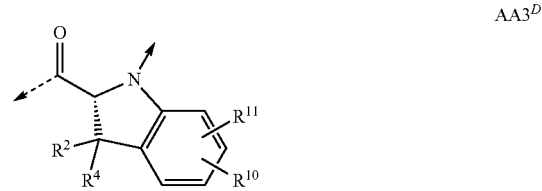

AA3$^D$

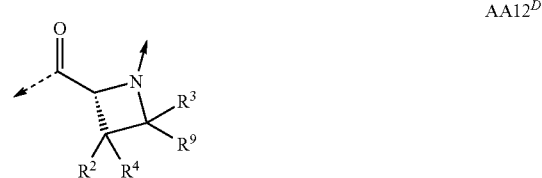

AA12$^D$ $T^2$ is an L α-amino acid residue of one of the formulae

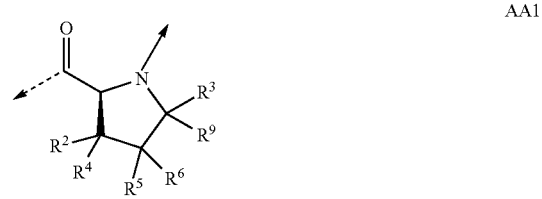

AA1

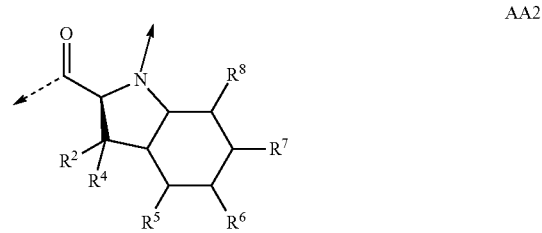

AA2

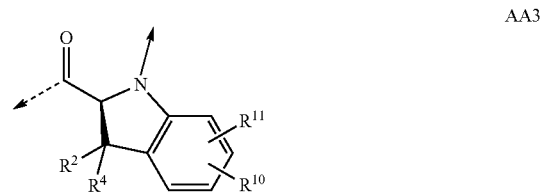

AA3

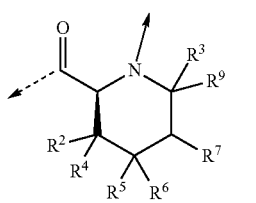
AA4
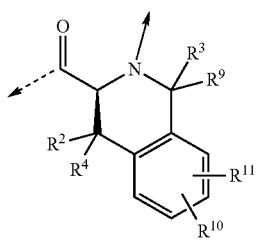
AA5
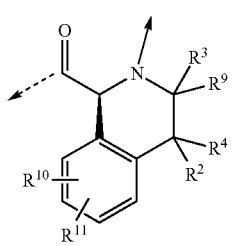
AA6
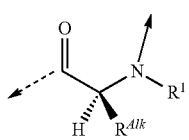
AA7
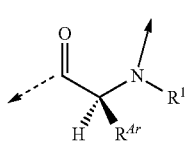
AA8
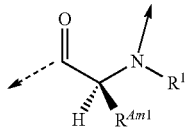
AA10$^a$
P$^1$ is an L α-amino acid residue of one of the formulae
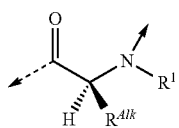
AA7
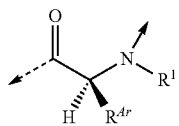
AA8
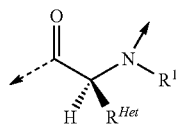
AA9
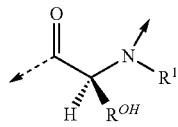
AA11
P$^2$ is an L α-amino acid residue of one of the formulae
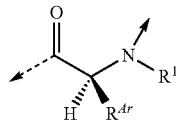
AA8
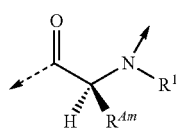
AA10
P$^3$, P$^8$ and P$^{10}$ are independently an L α-amino acid residue of one of the formulae
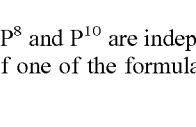
AA7
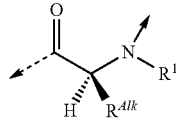
AA8
P$^4$ is an L α-amino acid residue of one of the formulae
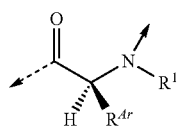
AA7
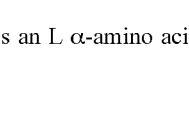
AA9
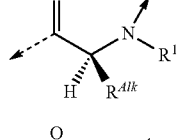
AA10

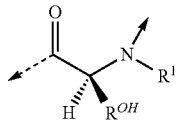

P⁵ is an L α-amino acid residue of one of the formulae

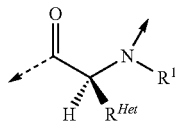
AA9

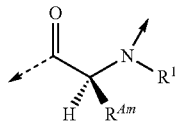
AA10

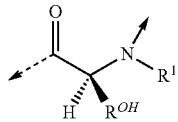
AA11

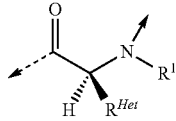
AA9

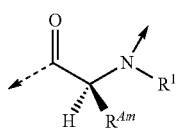
AA10

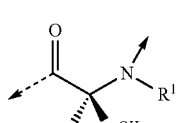
AA11

P⁶ is Gly; or an L or D α-amino acid residue of formula

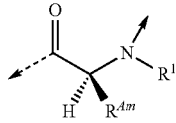
AA10

P⁷ is an L α-amino acid residue of formula

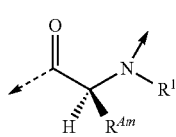
AA10

P⁹, P¹¹, and P¹² are independently an L α-amino acid residue of one of the formulae

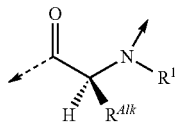
AA7

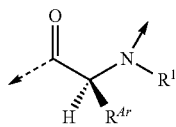
AA8

P² and P¹¹ taken together and/or P⁴ and P⁹ taken together can form interstrand linking bis(amino acid)-structures of one or the formulae

AA13

AA13$^D$ based on the linkage of two L- or D-α-amino acid residues;

$R^{Alk}$ is, with the proviso of containing less than 26 carbon- and/or heteroatoms, $C_{1-12}$-alkyl; $C_{2-12}$-alkenyl; cycloalkyl; cycloalkyl-$C_{1-6}$-alkyl; or $C_{1-6}$-alkoxy-$C_{1-6}$-alkyl;

$R^{Ar}$ is, with the proviso of containing less than 26 carbon- and/or heteroatoms, $—(CR^1R^4)_nR^{19}$; $—(CH_2)_q O(CH_2)_m R^{19}$; $—(CH_2)_n S(CH_2)_m R^{19}$; or $—(CH_2)_n NR^{14}(CH_2)_m R^{19}$;

$R^{Am}$ is, with the proviso of containing less than 26 carbon- and/or heteroatoms, $—(CR^1R^{13})_q NR^{15}R^{16}$; $—(CH_2)_q C(=NR^{13})NR^{15}R^{16}$; $—(CH_2)_q C(=NOR^{17})NR^{15}R^{16}$; $—(CH_2)_q C(=NNR^{15}R^{16})NR^{17}R^{18}$; $—(CR^1R^{13})_q NR^2 C(=NR^{17})NR^{15}R^{16}$; $—(CR^1R^{13})_q N=C(NR^{15}R^{16})NR^1R^{18}$; $—(CH_2)_n O(CH_2)_m NR^{15}R^{16}$; $—(CH_2)_n O(CH_2)_m C(=NR^{17})NR^{15}R^{16}$; $—(CH_2)_n O(CH_2)_m C(=NOR^{17})NR^{15}R^{16}$; $—(CH_2)_n O(CH_2)_m C(=NNR^{15}R^{16})NR^{17}R^{18}$; $—(CH_2)_n O(CH_2)_m NR^1 C(=NR^{17})NR^{15}R^{16}$; $—(CH_2)_n O(CH_2)_m N=C(NR^{15}R^{16})NR^{17}R^{18}$; $—(CH_2)_n S(CH_2)_m NR^{15}R^{16}$; $—(CH_2)_n S(CH_2)_m C(=NR^{17})NR^{15}R^{16}$; $—(CH_2)_n S(CH_2)_m C(=NOR^{17})NR^{15}R^{16}$; $—(CH_2)_n S(CH_2)_m C(=NNR^{15}R^{16})NR^{17}R^{18}$; $—(CH_2)_n S(CH_2)_m NR^1 C(=NR^{17})NR^{15}R^{16}$; or $—(CH_2)_n S(CH_2)_m N=C(NR^{15}R^{16})NR^{17}R^{18}$;

$R^{Am1}$ is, with the proviso of containing less than 26 carbon- and/or heteroatoms, $-(CR^1R^{13})_q NR^{15}R^{16}$;

$R^{Het}$ is, with the proviso of containing less than 26 carbon- and/or heteroatoms, $-(CR^1R^{13})_q OR^{14}$; $-(CR^1R^{13})_q SR^{15}$; $-(CR^1R^{13})_q SO_2R^{15}$; $-(CR^1R^{13})_q SO_2NR^1R^{14}$; $-(CR^1R^{13})_q SO_2NR^{15}R^{16}$; $-(CR^1R^{13})_q NR^{14}SO_2R^{15}$; $-(CR^1R^{13})_q NR^{14}SO_2NR^{15}R^{16}$; $-(CH_2)_n O(CH_2)_m OR^{14}$; $-(CH_2)_n O(CH_2)_m SR^{15}$; $-(CR^1R^{13})_q COOR^{15}$; $-(CR^1R^{13})_q CONR^{15}R^{16}$; $-(CR^1R^{13})_q NR^{15}R^{27}$; or $-(CR^1R^{13})_q NR^2CONR^{15}R^{16}$;

$R^{OH}$ is, with the proviso of containing less than 26 carbon- and/or heteroatoms, $-(CR^1R^{13})_q OH$; $-(CR^1R^{13})_q SH$; $-(CH_2)_n O(CH_2)_m OH$; $-(CH_2)_n S(CH_2)_m OH$; $-(CH_2)_n NR^1(CH_2)_m OH$; hydroxy-$C_{1-8}$-alkyl; hydroxy-$C_{2-8}$-alkenyl; hydroxy-cycloalkyl; or hydroxy-heterocycloalkyl;

Z is, with the proviso of containing less than 25 carbon- and/or heteroatoms, $-(CH_2)_n-S-S-(CH_2)_m-$; $-(CH_2)_n CH=CH(CH_2)_m-$; $-(CH_2)_n CONR^1(CH_2)_m-$; $-(CH_2)_n NR^1 CO(CH_2)_m-$; or $-(CH_2)_n NR^1 CONR^2(CH_2)_m-$;

$R^1$, $R^2$ and $R^3$ are independently
  H; $CF_3$; $C_{1-8}$-alkyl; $C_{2-8}$-alkenyl; or aryl-$C_{1-6}$-alkyl;

$R^4$, $R^5$, $R^6$, $R^7$ and $R^8$ are independently
  H; F; $CF_3$; $C_{1-8}$-alkyl; $C_{2-8}$-alkenyl; cycloalkyl; heterocycloalkyl; aryl; heteroaryl; aryl-$C_{1-6}$-alkyl; heteroaryl-$C_{1-6}$-alkyl; $-(CHR^{13})_o OR^{15}$; $-O(CO)R^{15}$; $-(CHR^{13})_o SR^{15}$; $-(CHR^{13})_o NR^{15}R^{16}$; $-(CHR^{13})_o OCONR^{15}R^{16}$; $-(CHR^{13})_o NR^1 CONR^{15}R^{16}$; $-(CHR^{13})_o NR^1 COR^{15}$; $-(CHR^{13})_o COOR^{15}$; $-(CHR^{13})_o CONR^{15}R^{16}$; $-(CHR^{13})_o PO(OR^1)_2$; $-(CHR^{13})_o SO_2R^{15}$; $-(CHR^{13})_o NR^1 SO_2R^{15}$; $-(CHR^{13})_o SO_2NR^{15}R^{16}$; $-(CR^1R^{13})_o R^{23}$; or $-(CHR^1)_n O(CHR^2)_m R^{23}$; or $R^4$ and $R^2$; or $R^5$ and $R^6$ taken together can form:
  $=O$; $=NR^1$; $=NOR^1$; $=NOCF_3$; or $-(CHR^1)-$;

$R^4$ and $R^5$; $R^6$ and $R^7$; $R^7$ and $R^8$; or $R^6$ and $R^9$ taken together can form:
  $-(CHR^1)_p-$; $-(CH_2)_n O(CH_2)_m-$; $-(CH_2)_n S(CH_2)_m-$; or $-(CH_2)_n NR^1(CH_2)_m-$;

$R^9$ is H; F; $CF_3$; $C_{1-8}$-alkyl; $C_{2-8}$-alkenyl; cycloalkyl; heterocycloalkyl; aryl; heteroaryl; aryl-$C_{1-6}$-alkyl; heteroaryl-$C_{1-6}$-alkyl; $-(CHR^{13})_r OR^{15}$; $-O(CO)R^{15}$; $-(CHR^{13})_r SR^{15}$; $-(CHR^{10})_r NR^{15}R^{16}$; $-(CHR^{13})_r OCONR^{15}R^{16}$; $-(CHR^{13})_r NR^1 CONR^{15}R^{16}$; $-(CHR^{13})_r NR^1 COR^{15}$; $-(CHR^{13})_o COOR^{15}$; $-(CHR^{13})_o CONR^{15}R^{16}$; $-(CHR^{13})_o PO(OR^1)_2$; $-(CHR^{13})_r SO_2R^{15}$; $-(CHR^{13})_r NR^1 SO_2R^{15}$; $-(CHR^{13})_r SO_2NR^{15}R^{16}$; $-(CR^1R^{13})_o R^{23}$; or $-(CHR^1)_r O(CHR^1)_o R^{23}$;

$R^{10}$, $R^{11}$ and $R^{12}$ are independently
  H; F; Cl; Br; I; $CF_3$; $OCF_3$; $OCHF_2$; CN; $NO_2$; $C_{1-8}$-alkyl; $C_{2-8}$-alkenyl; aryl; heteroaryl; aryl-$C_{1-6}$-alkyl; heteroaryl-$C_{1-6}$-alkyl; $-(CHR^{13})_o OR^{15}$; $-O(CO)R^{15}$; $-(CHR^{13})_o SR^{15}$; $-(CHR^{13})_o NR^{15}R^{16}$; $-(CHR^{13})_o OCONR^{15}R^{16}$; $-(CHR^{13})_o NR^1 CONR^{15}R^{16}$; $-(CHR^{13})_o NR^1 COR^{15}$; $-(CHR^{13})_o COOR^{15}$; $-(CHR^{13})_o CONR^{15}R^{16}$; $-(CHR^{13})_o PO(OR^1)_2$; $-(CHR^{13})_o SO_2R^{15}$; $-(CHR^{13})_o NR^1 SO_2R^{15}$; $-(CHR^{13})_o SO_2NR^{15}R^{16}$; or $-(CR^1R^{13})_o R^{23}$;

$R^{13}$ is H; F; $CF_3$; $C_{1-8}$-alkyl; $C_{2-8}$-alkenyl; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; $-(CHR^1)_o OR^{15}$; $-OCOR^1$; $-(CHR^1)_o NR^{15}R^{16}$; $-COOR^{15}$; $-CONR^{15}R^{16}$; $-SO_2R^{15}$; or $-SO_2NR^{15}R^{16}$;

$R^{14}$ is H; $CF_3$; $C_{1-8}$-alkyl; $C_{2-8}$-alkenyl; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; heteroaryl-heterocycloalkyl; $-(CHR^1)_o OR^{15}$; $-(CHR^1)_o SR^{15}$; $-(CHR^1)_o NR^{15}R^{16}$; $-(CHR^1)_o COOR^{15}$; $-(CHR^1)_o CONR^{15}R^{16}$; or $-(CHR^1)_o SO_2R^{15}$;

$R^{15}$, $R^{16}$, $R^{17}$ and $R^{18}$ are independently

H; $C_{1-8}$-alkyl; $C_{2-8}$-alkenyl; $C_{1-6}$-alkoxy; cycloalkyl; heterocycloalkyl; cycloalkyl-$C_{1-6}$-alkyl; heterocycloalkyl-$C_{1-6}$-alkyl; aryl; heteroaryl; aryl-$C_{1-6}$-alkyl; heteroaryl-$C_{1-6}$-alkyl; cycloalkyl-aryl; heterocycloalkyl-aryl; cycloalkyl-heteroaryl; heterocycloalkyl-heteroaryl; aryl-cycloalkyl; aryl-heterocycloalkyl; heteroaryl-cycloalkyl; or heteroaryl-heterocycloalkyl; or the structural elements $-NR^{15}R^{16}$ and $-NR^{17}R^{18}$ can independently form: heterocycloalkyl; aryl-heterocycloalkyl; or heteroaryl-heterocycloalkyl;

$R^{19}$ is an aryl group of one of the formulae

AR1

AR2 or a group of one of the formulae

H1

H2

H3

H4

H5

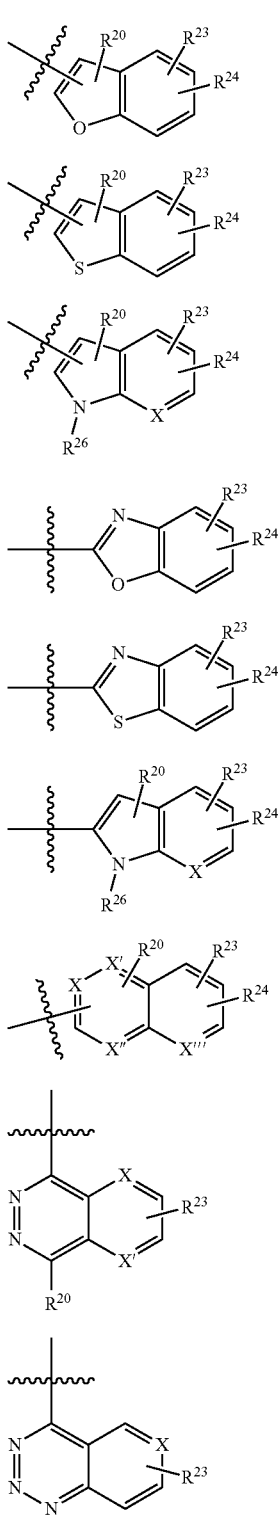

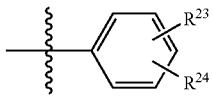

X, X', X" and X'" are independently
—CR$^{20}$; or N;

R$^{20}$ and R$^{21}$ are independently
H; F; Cl; Br; I; OH; NH$_2$; NO$_2$; CN; CF$_3$; OCHF$_2$; OCF$_3$; C$_{1-8}$-alkyl; C$_{2-8}$-alkenyl; aryl; heteroaryl; aryl-C$_{1-6}$-alkyl; heteroaryl-C$_{1-6}$-alkyl; —(CH$_2$)$_o$R$^{22}$; —(CH$_2$)$_o$OR$^{15}$; —O(CO)R$^{15}$; —O(CH$_2$)$_o$R$^{22}$; —(CH$_2$)$_o$SR$^{15}$; —(CH$_2$)$_o$NR$^{15}$R$^{16}$; —(CH$_2$)$_o$OCONR$^{15}$R$^{16}$; —(CH$_2$)$_o$NR$^1$CONR$^{15}$R$^{16}$; —(CH$_2$)$_o$NR$^1$COR$^{15}$; —(CH$_2$)$_o$COOR$^{15}$; —(CH$_2$)$_o$CONR$^{15}$R$^{16}$; —(CH$_2$)$_o$PO(OR$^1$)$_2$; —(CH$_2$)$_o$SO$_2$R$^{14}$; or —(CH$_2$)$_o$COR$^{15}$;

R$^{22}$ is an aryl group of the formula

R$^{23}$, R$^{24}$ and R$^{25}$ are independently
H; F; Cl; Br; I; OH; NH$_2$; NO$_2$; CN; CF$_3$; OCHF$_2$; OCF$_3$; C$_{1-8}$-alkyl; C$_{2-8}$-alkenyl; —(CH$_2$)$_o$OR$^{15}$; —O(CO)R$^{15}$; —(CH$_2$)$_o$NR$^1$R$^{15}$; —(CH$_2$)$_o$COOR$^{15}$; —(CH$_2$)$_o$CONR$^1$R$^{15}$;

R$^{26}$ is H; Ac; C$_{1-8}$-alkyl; or aryl-C$_{1-6}$-alkyl;
R$^{27}$ is —CO(CR$^1$R$^{13}$)$_q$R$^{15}$;
n and m are independently an integer of 0-5 with the proviso that n+m<6;
o is 0-4; p is 2-6; q is 1-6; and r is 1-3;
or a pharmaceutically acceptable salt thereof;
and with the proviso that
if no interstrand linkage is formed;
and
T$^1$ is an D α-amino acid residue of one of the formulae AA1$^D$; AA2$^D$; or AA3$^D$;
then
T$^2$ is an L α-amino acid residue of AA7; AA8; or AA10$^a$.

Each single group "R$^x$" with the same index-number x for x=1-27 is independently selected on each occurrence in a specific formula and, therefore, they can be the same or different.

As used in this description, the term "alkyl", taken alone or in combinations (i.e. as part of another group, such as "aryl-C$_{1-6}$-alkyl") designates saturated, straight-chain or branched hydrocarbon radicals and may be optionally substituted. The term "C$_{x-y}$-alkyl" (x and y each being an integer) refers to an alkyl group as defined before containing x to y carbon atoms. For example a C$_{1-6}$-alkyl group contains one to six carbon atoms. Representative examples of alkyl groups include methyl, ethyl, n-propyl, iso-propyl, n-butyl, iso-butyl, sec-butyl, tert-butyl, n-pentyl, n-hexyl and the like.

The term "alkenyl", taken alone or in combinations, designates straight chain or branched hydrocarbon radicals containing at least one or, depending on the chain length, up to four olefinic double bonds. Such alkenyl moieties are optionally substituted and can independently exist as E or Z configurations per double bond, which are all part of the invention. The term "C$_{x-y}$-alkenyl" (x and y each being an integer) refers to an alkenyl group as defined before containing x to y carbon atoms.

The term "cycloalkyl", taken alone or in combinations, refers to a saturated or partially unsaturated alicyclic moiety having from three to ten carbon atoms and may be optionally substituted. Examples of this moiety include, but are not limited to, cyclohexyl, norbornyl, decalinyl and the like.

The term "heterocycloalkyl", taken alone or in combinations, describes a saturated or partially unsaturated mono- or bicyclic moiety having from three to nine ring carbon atoms and one or more ring heteroatoms selected from nitrogen, oxygen or sulphur. This term includes, for example, morpholino, piperazino, azetidinyl, pyrrolidinyl, tetrahydrofuranyl, piperidinyl, octahydro-1H-indolyl, 1,7-diazaspiro[4.4] nonyl and the like. Said heterocycloalkyl ring(s) might be optionally substituted.

The term "aryl", taken alone or in combinations, designates aromatic carbocyclic hydrocarbon radicals containing one or two six-membered rings, such as phenyl or naphthyl, which may be optionally substituted by up to three substituents such as Br, Cl, F, $CF_3$, OH, $OCF_3$, $OCHF_2$, $NH_2$, $N(CH_3)_2$, $NO_2$, CN, $C_{1-6}$-alkyl, $C_{2-6}$-alkenyl, phenyl or phenoxy.

The term "heteroaryl", taken alone or in combinations, designates aromatic heterocyclic radicals containing one or two five- and/or six-membered rings, at least one of them containing up to three heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "aryl-$C_{x-y}$-alkyl", as used herein, refers to an $C_{x-y}$-alkyl group as defined above, substituted by an aryl group, as defined above. Representative examples of aryl-$C_x$-alkyl moieties include, but are not limited to, benzyl, 1-phenylethyl, 2-phenylethyl, 3-phenylpropyl, 2-phenylpropyl and the like.

The term "heteroaryl-$C_{x-y}$-alkyl", as used herein, refers to an $C_{x-y}$-alkyl group as defined above, substituted by a heteroaryl group, as defined above. Examples of heteroaryl-$C_{x-y}$-alkyl groups include pyridin-3-ylmethyl, (1H-pyrrol-2-yl)ethyl and the like.

The term "aryl-cycloalkyl", as used herein, refers to a cycloalkyl group as defined above, substituted or annelated by an aryl group, as defined above. Examples of aryl-cycloalkyl moieties include, but are not limited to, phenylcyclopentyl, 2,3-dihydro-1H-indenyl, 1,2,3,4-tetrahydronaphthalenyl and the like.

The term "aryl-heterocycloalkyl", as used herein, refers to a heterocycloalkyl group as defined above, substituted or annelated by an aryl group, as defined above. Examples of aryl-heterocycloalkyl moieties include, but are not limited to, indolinyl, 1,2,3,4-tetrahydroquinolinyl and the like.

The term "heteroaryl-cycloalkyl", as used herein, refers to a cycloalkyl group as defined above, substituted or annelated by a heteroaryl group, as defined above. Examples of heteroaryl-cycloalkyl moieties include, but are not limited to, 5,6,7,8-tetrahydroquinolinyl and the like.

The term "heteroaryl-heterocycloalkyl", as used herein, refers to a heterocycloalkyl group as defined above, substituted or annelated by a heteroaryl group, as defined above. Examples of heteroaryl-heterocycloalkyl moieties include, but are not limited to, 4-(thiazol-2-yl)piperazinyl, 5,6,7,8-tetrahydro-1,6-naphthyridinyl and the like.

The terms "cycloalkyl-aryl", "heterocycloalkyl-aryl", "cycloalkyl-heteroaryl", and "heterocycloalkyl-heteroaryl", as used herein, are defined analogously to the terms "aryl-cycloalkyl", "aryl-heterocycloalkyl", "heteroaryl-cycloalkyl" and "heteroaryl-heterocycloalkyl", as defined above, but connected in the opposite direction, e.g. instead of 4-(thiazol-2-yl)piperazinyl the term refers to 2-(piperazin-1-yl)thiazolyl and the like.

The terms "hydroxy", "alkoxy" and "aryloxy", taken alone or in combinations, refer to the groups of —OH, —O-alkyl and —O-aryl respectively, wherein an alkyl group or an aryl group is as defined above. The term "$C_{x-y}$-alkoxy" (x and y each being an integer) refers to an —O-alkyl group as defined before containing x to y carbon atoms attached to an oxygen atom. Representative examples of alkoxy groups include methoxy, ethoxy, n-propoxy, iso-propoxy, n-butoxy, tert-butoxy and the like. Examples of aryloxy include e.g. phenoxy. For avoidance of doubt e.g. the term "hydroxy-$C_{1-8}$-alkyl" represents, among others, groups like e.g. hydroxymethyl, 1-hydroxypropyl, 2-hydroxypropyl or 3-hydroxy-2,3-dimethylbutyl.

The term "optionally substituted" is in general intended to mean that a group, such as, but not limited to $C_{x-y}$-alkyl, $C_{x-y}$-alkenyl, cycloalkyl, aryl, heteroaryl, heterocycloalkyl, $C_{x-y}$-alkoxy and aryloxy may be substituted with one or more substituents independently selected from amino (—$NH_2$), dimethylamino, nitro (—$NO_2$), halogen (F, Cl, Br, I), $CF_3$, cyano (—CN), hydroxy, methoxy, ethoxy, phenyloxy, benzyloxy, acetoxy, oxo (=O), carboxy, carboxamido, methyl, ethyl, phenyl, benzyl, sulfonic acid, sulfate, phosphonic acid, phosphate, or phosphonate.

In the context of this invention the term "naturally or non-naturally occurring α-amino acid" typically comprises any natural α-amino acid, such as the proteogenic amino acids (examples listed below), their natural or semi-synthetic derivatives as well as α-amino acids of purely synthetic origin. This term includes as well α-amino acids which are optionally substituted at the α-nitrogen of the amino acid such as, but not limited to, acetylation or alkylation, e.g. methylation, or benzylation.

The term "aliphatic α-amino acid" refers to α-amino acids with an aliphatic side-chain, such as, but not limited to, alanine, valine, leucine, isoleucine, n-octylglycine etc.

The term "aromatic α-amino acid" refer to α-amino acids with a side-chain comprising an aromatic or heteroaromatic group, such as, but not limited to, phenylalanine, tryptophan, histidine, O-methyl-tyrosine, 4-trifluormethyl-phenylalanine, 3,4-dichloro-homophenylalanine etc.

The term "basic α-amino acid" refers to α-amino acids with a side-chain comprising at least one amino group, such as, but not limited to, lysine, ornithine etc. and further substituted derivatives thereof. The aforesaid amino group can be substituted by amidino groups to form α-amino acids, such as, but not limited to, arginine, homoarginine etc. and further substituted derivatives thereof, or by diamino methylidine groups.

The term "cross-linking α-amino acid" refers to α-amino acids with a side-chain comprising a function able to cross-link to a second α-amino acid by a covalent bond, such as, but not limited to, cysteine, homocysteine etc.

The term "alcoholic α-amino acid" refers to α-amino acids with a side-chain comprising an alcoholic or thioalcoholic group, i.e. a hydroxy or sulfhydryl function, such as, but not limited to, serine, threonine etc.

For the avoidance of doubt the term "single side-chain" in the context of an α-amino acid refers to a structure where the α-carbon of the amino acid is covalently connected to the (in-chain) groups of the carbonyl (C=O) and nitrogen (N) as well as to one hydrogen (H) and one variable side-chain, e.g. as defined above. A "single side-chain" may include as well a heterocyclic structure comprising the α-amino atom, such as but not limited to, proline, pipecolic acid etc.

For the avoidance of doubt the term "heteroatom" refers to any atom that is not carbon or hydrogen.

The descriptors L respectively D refer to the stereochemistry at the α-position of an α-amino acid and are used according the Fischer-Rosanoff convention of the IUPAC.

The peptidomimetics of the present invention can also be diastereomers (e.g. epimers) of compounds of formula (I) if no specific stereochemistry of the chiral center is determined in the description. These stereoisomers can be prepared by a modification of the process described below in which the appropriate isomers (e.g. epimers/enantiomers) of chiral starting materials are used. In case of ambiguous stereochemistry in the above description each single epimer is part of the present invention as well as a mixture of both.

A further embodiment of the present invention may also include compounds, which are identical to the compounds of formula (I), except that one or more atoms are replaced by an atom having an atomic mass number or mass different from the atomic mass number or mass usually found in nature, e.g. compounds enriched in $^2$H (D), $^3$H, $^{11}$C, $^{14}$C, $^{127}$I etc. These isotopic analogs and their pharmaceutical salts and formulations are considered useful agents in the therapy and/or diagnostic, for example, but not limited to, where a fine-tuning of in vivo half-life time could lead to an optimized dosage regimen.

A further particular embodiment of the invention relates to derivatives of general formula (I), wherein specifically
$T^1$ is the D α-amino acid residue AA1$^D$; AA12$^D$; AA7$^D$; AA8$^D$; AA10$^D$; or AA11$^D$;
$T^2$ is an L α-amino acid residue of one of the formulae AA1; AA7; AA8; or AA10$^a$;
or a pharmaceutically acceptable salt thereof.

An alternative particular embodiment of the invention relates to derivatives of general formula (I), wherein specifically
$P^1$ is an L α-amino acid residue of one of the formulae AA7; or AA8;
$P^2$ is an L α-amino acid residue of one of the formulae AA8; or AA10
$P^5$ is an L α-amino acid residue of formula AA10; or AA11;
$P^6$ is Gly; or an D or L α-amino acid residue of formula AA10;
$P^9$ is an L α-amino acid residue of one of the formulae AA7; AA8; AA10; or AA11;
$P^{11}$ is an L α-amino acid residue of one of the formulae AA7; AA9; AA10; or AA11;
$P^{12}$ is an L α-amino acid residue of one of the formulae AA7; AA8; AA10; or AA11;
$P^2$ and $P^{11}$ taken together and/or $P^4$ and $P^9$ taken together can form interstrand linking bis(amino acid)-structures of one of the formulae AA13; or AA13$^D$;
or a pharmaceutically acceptable salt thereof.

In another particular embodiment of the invention the elements of general formula (I) are defined as follows
$T^1$ is $^D$Pro; $^D$Azt; or $^D$Tic;
$T^2$ is Pro; Pic; Oic; Tic; Ala; Abu; Leu; Ile; Val; Nva; NMeAla; NMeAbu; NMeLeu; NMeIle; NMeVal; Tyr; Phe; Trp; Dab; Dap; Orn; or Lys;
$P^1$ is Ala; Abu; Leu; Ile; Val; Nva; Nle; Cpa; Cpg; Phe; Tyr; or Trp;
$P^2$ is Tyr; Phe; Trp; Dab; Dap; Orn; Lys; or Arg;
$P^3$ is Val; tBuGly; Ala; Leu; Ile; Val; Nva; Tyr; Phe; or Trp;
$P^4$ is Ala; Val; Abu; Leu; Ile; Nva; Dab; Dap; Orn; Lys; Arg; Asn; Gln; Thr; alloThr; Ser; or Hse;
$P^5$ is Orn; Dap; Dab; Lys; Arg; Thr; alloThr; Ser; or Hse;
$P^6$ is Gly; Dab; $^D$Dab; Dap; $^D$Dap; Orn; $^D$Orn; Lys; $^D$Lys; Arg; or $^D$Arg;
$P^7$ is Dab; Dap; Orn; Lys; or Arg;
$P^8$ is Trp; Phe; Tyr; Phg; Leu; Ile; Val; Nva; Abu; or Ala;
$P^9$ is Ala; Abu; Leu; Ile; Val; Nva; Tyr; Phe; Trp; Dab; Dap; Orn; Lys; Arg; Ser; Thr; alloThr; or Hse;
$P^{10}$ is Val; tBuGly; Ala; Leu; Ile; Nva; Abu; Chg; Phg; Tyr; Phe; or Trp;
$P^{11}$ is Ala; Val; Abu; Nva; Leu; Ile; Ser; Thr; alloThr; Hse; Asn; Gln; Asp; Glu; Dab; Dap; Orn; Lys; or Arg;
$P^{12}$ is Val; Ala; Abu; Nva; Leu; Ile; Tyr; His; Phe; Trp; Dab; Dap; Orn; Lys; Arg; Ser; Thr; alloThr; or Hse;
$P^2$ and $P^{11}$ taken together and/or $P^4$ and $P^9$ taken together can form interstrand linking bis(amino acid)-structures based on the linkage of two L- or D-amino acid residues following
connection of the side chain of Cys; or Hcy; with the side chain of Cys; or Hcy; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;
or a pharmaceutically acceptable salt thereof;
with proviso that
if no interstrand linkage is formed;
and
T is $^D$Pro; or $^D$Tic;
then
$T^2$ is Ala; Abu; Leu; Ile; Val; Nva; NMeAla; NMeAbu; NMeLeu; NMeIle; NMeVal; Tyr; Phe; Trp; Dab; Dap; Orn; or Lys.

In another particular embodiment of the invention the elements of general formula (I) are defined as follows
T is $^D$Pro; or $^D$Azt;
$T^2$ is Pro; Ala; Leu; NMeAla; Tyr; Phe; Dab; Dap; Orn; or Lys;
$P^1$ is Leu; Ile; Val; Cpa; Cpg; Phe; or Trp;
$P^2$ is Tyr; Dab; Dap; or Lys;
$P^3$ is Val; tBuGly; or Tyr;
$P^4$ is Ala; Val; Dab; Arg; Asn; or Thr;
$P^5$ is Orn; Dap; Dab; or Thr;
$P^6$ is Gly; Dab; or $^D$Dab;
$P^7$ is Dab;
$P^8$ is Trp; Phe; or Leu;
$P^9$ is Ala; Tyr; Dab; Dap; Ser; or Thr;
$P^{10}$ is Val; tBuGly; Chg; Phg; or Tyr;
$P^{11}$ is Ala; Val; Ser; Thr; Asp; Glu; Dap; Dab; or Lys;
$P^{12}$ is Val; Tyr; His; Dab; Ser; or Thr;
$P^2$ and $P^{11}$ taken together and/or $P^4$ and $P^9$ taken together can form interstrand linking bis(amino acid)-structures based on the linkage of two L- or D-amino acid residues following
connection of the side chain of Cys; or Hcy; with the side chain of Cys; or Hcy; by a disulfide linkage; or
connection of the side chain of Dap; Dab; or Lys; with the side chain of Asp; or Glu; by a lactam linkage; or
connection of the side chain of Dap; or Dab; with the side chain of Dap; or Dab; by an urea linkage;
or a pharmaceutically acceptable salt thereof;
with the proviso that
if no interstrand linkage is formed;
and
$T^1$ is $^D$Pro;
then
$T^2$ is Ala; Leu; NMeAla; Tyr; Phe; Dab; Dap; Orn; or Lys.

In a further particular embodiment of the invention the elements of general formula (I) are defined as follows
$T^1$ is $^D$Pro; or $^D$Azt;
$T^2$ is Pro; Leu; NMeAla; Tyr; Phe; Dab; Dap; Orn; or Lys;
$P^1$ is Leu; Ile; Val; Phe; or Trp;
$P^2$ is Dab; Dap; or Lys;
$P^3$ is Tyr;
$P^4$ is Ala; Dab; or Arg;
$P^5$ is Orn; Dap; Dab; or Thr;
$P^6$ is Dab; or $^D$Dab;
$P^7$ is Dab;
$P^8$ is Trp; or Leu;
$P^9$ is Ala; or Dab;

P¹⁰ is Val; tBuGly; or Phg;
P¹¹ is Ala; Ser; Asp; Glu; Dap; Dab, or Lys;
P¹² is Val; Tyr; His; Ser; or Thr;
P² and P¹¹ taken together and/or P⁴ and P⁹ taken together can form interstrand linking bis(amino acid)-structures based on the linkage of two L- or D-amino acid residues following
  connection of the side chain of Cys; or Hcy; with the side chain of Cys; or Hcy; by a disulfide linkage; or
  connection of the side chain of Dap; Dab; or Lys; with the side chain of Asp; or Glu; by a lactam linkage; or
  connection of the side chain of Dap; with the side chain of Dap; by an urea linkage;
or a pharmaceutically acceptable salt thereof;
with the proviso that
if no interstrand linkage is formed;
and
T¹ is ᴰPro;
then
T² is Leu; NMeAla; Tyr; Phe; Dab; Dap; Orn; or Lys.

In another further particular embodiment of the invention the elements of general formula (I) are defined as follows
T¹ is ᴰPro; ᴰAzt; or ᴰTic;
T² is Pro; Pic; Oic; Tic; Ala; Abu; Leu; Ile; Val; Nva; NMeAla; NMeAbu; NMeLeu; NMeIle; NMeVal; Tyr; Phe; Trp; Dab; Dap; Orn; or Lys;
P¹ is Ala; Abu; Leu; Ile; Val; Nva; Nle; Cpa; Cpg; Phe; Tyr; or Trp;
P² is Tyr; Phe; Trp; Dab; Dap; Orn; Lys; or Arg;
P³ is Val; tBuGly; Ala; Leu; Ile; Val; Nva; Tyr; Phe; or Trp;
P⁴ is Ala; Val; Abu; Leu; Ile; Nva; Dab; Dap; Orn; Lys; Arg; Asn; Gln; Thr; alloThr; Ser; or Hse;
P⁵ is Orn; Dap; Dab; Lys; Arg; Thr; alloThr; Ser; or Hse;
P⁶ is Gly; Dab; ᴰDab; Dap; ᴰDap; Orn; ᴰOrn; Lys; ᴰLys; Arg; or ᴰArg;
P⁷ is Dab; Dap; Orn; Lys; or Arg;
P⁸ is Trp; Phe; Tyr; Phg; Leu; Ile; Val; Nva; Abu; or Ala;
P⁹ is Ala; Abu; Leu; Ile; Val; Nva; Tyr; Phe; Trp; Dab; Dap; Orn; Lys; Arg; Ser; Thr; alloThr; or Hse;
P¹⁰ is Val; tBuGly; Ala; Leu; Ile; Nva; Abu; Chg; Phg; Tyr; Phe; or Trp;
P¹¹ is Ala; Val; Abu; Nva; Leu; Ile; Ser; Thr; alloThr; Hse; Asn; Gln; Asp; Glu; Dab; Dap; Orn; Lys; or Arg;
P¹² is Val; Ala; Abu; Nva; Leu; Ile; Tyr; His; Phe; Trp; Dab; Dap; Orn; Lys; Arg; Ser; Thr; alloThr; or Hse;
P² and P¹¹ taken together and/or P⁴ and P⁹ taken together form interstrand linking bis(amino acid)-structures based on the linkage of two L- or D-amino acid residues following
  connection of the side chain of Cys; or Hcy; with the side chain of Cys; or Hcy; by a disulfide linkage; or
  connection of the side chain of Dap; Dab; Orn; or Lys; with the side chain of Asp; Glu; or hGlu; by a lactam linkage; or
  connection of the side chain of Dap; Dab; or Orn; with the side chain of Dap; Dab; or Orn; by an urea linkage;
or a pharmaceutically acceptable salt thereof.

In another particular embodiment of the invention the elements of general formula (I) are defined as follows
T¹ is ᴰPro; or ᴰAzt;
T² is Pro; Ala; Leu; NMeAla; Tyr; Phe; Dab; Dap; Orn; or Lys;
P¹ is Leu; Ile; Val; Cpa; Cpg; Phe; or Trp;
P² is Tyr; Dab; Dap; or Lys;
P³ is Val; tBuGly; or Tyr;
P⁴ is Ala; Val; Dab; Arg; Asn; or Thr;
P⁵ is Orn; Dap; Dab; or Thr;
P⁶ is Gly; Dab; or ᴰDab;
P⁷ is Dab;
P⁸ is Trp; Phe; or Leu;
P⁹ is Ala; Tyr; Dab; Dap; Ser; or Thr;
P¹⁰ is Val; tBuGly; Chg; Phg; or Tyr;
P¹¹ is Ala; Val; Ser; Thr; Asp; Glu; Dap; Dab; or Lys;
P¹² is Val; Tyr; His; Dab; Ser; or Thr;
P² and P¹¹ taken together and/or P⁴ and P⁹ taken together form interstrand linking bis(amino acid)-structures based on the linkage of two L- or D-amino acid residues following
  connection of the side chain of Cys; or Hcy; with the side chain of Cys; or Hcy; by a disulfide linkage; or
  connection of the side chain of Dap; Dab; or Lys; with the side chain of Asp; or Glu; by a lactam linkage; or
  connection of the side chain of Dap; or Dab; with the side chain of Dap; or Dab; by an urea linkage;
or a pharmaceutically acceptable salt thereof.

In another further particular embodiment of the invention the elements of general formula (I) are defined as follows
T¹ is ᴰPro; or ᴰAzt;
T² is Pro; NMeAla; Tyr; Dab; Dap; Orn; or Lys;
P¹ is Leu; Ile; Val; Phe; or Trp;
P² is Dab; Dap; or Lys;
P³ is Tyr;
P⁴ is Ala; Dab; or Arg;
P⁵ is Orn; Dap; Dab; or Thr;
P⁶ is Dab; or ᴰDab;
P⁷ is Dab;
P⁸ is Trp; or Leu;
P⁹ is Ala; or Dab;
P¹⁰ is Val; tBuGly; or Phg;
P¹¹ is Ala; Ser; Asp; Glu; Dap; Dab, or Lys;
P¹² is Val; Tyr; His; Ser; or Thr;
P² and P¹¹ taken together and/or P⁴ and P⁹ taken together form interstrand linking bis(amino acid)-structures based on the linkage of two L- or D-amino acid residues following
  connection of the side chain of Cys; or Hcy; with the side chain of Cys; or Hcy; by a disulfide linkage; or
  connection of the side chain of Dap; Dab; or Lys; with the side chain of Asp; or Glu; by a lactam linkage; or
  connection of the side chain of Dap; with the side chain of Dap; by an urea linkage;
or a pharmaceutically acceptable salt thereof.

In another further particular embodiment of the invention the elements of general formula (I) are defined as follows
T¹ is ᴰPro; ᴰAzt; or ᴰTic;
T² is Pro; Pic; Oic; Tic; Ala; Abu; Leu; Ile; Val; Nva; NMeAla; NMeAbu; NMeLeu; NMeIle; NMeVal; Tyr; Phe; Trp; Dab; Dap; Orn; or Lys;
P¹ is Ala; Abu; Leu; Ile; Val; Nva; Nle; Cpa; Cpg; Phe; Tyr; or Trp;
P² is Tyr; Phe; Trp; Dab; Dap; Orn; Lys; or Arg;
P³ is Val; tBuGly; Ala; Leu; Ile; Val; Nva; Tyr; Phe; or Trp;
P⁴ is Ala; Val; Abu; Leu; Ile; Nva; Dab; Dap; Orn; Lys; Arg; Asn; Gln; Thr; alloThr; Ser; or Hse;
P⁵ is Orn; Dap; Dab; Lys; Arg; Thr; alloThr; Ser; or Hse;
P⁶ is Gly; Dab; ᴰDab; Dap; ᴰDap; Orn; ᴰOrn; Lys; ᴰLys; Arg; or ᴰArg;
P⁷ is Dab; Dap; Orn; Lys; or Arg;
P⁸ is Trp; Phe; Tyr; Phg; Leu; Ile; Val; Nva; Abu; or Ala;
P⁹ is Ala; Abu; Leu; Ile; Val; Nva; Tyr; Phe; Trp; Dab; Dap; Orn; Lys; Arg; Ser; Thr; alloThr; or Hse;
P¹⁰ is Val; tBuGly; Ala; Leu; Ile; Nva; Abu; Chg; Phg; Tyr; Phe; or Trp;

P¹¹ is Ala; Val; Abu; Nva; Leu; Ile; Ser; Thr; alloThr; Hse; Asn; Gln; Asp; Glu; Dab; Dap; Orn; Lys; or Arg;
P¹² is Val; Ala; Abu; Nva; Leu; Ile; Tyr; His; Phe; Trp; Dab; Dap; Orn; Lys; Arg; Ser; Thr; alloThr; or Hse;
or a pharmaceutically acceptable salt thereof;
with the proviso that
if T¹ is ᴰPro; or ᴰTic;
then
T² is Ala; Abu; Leu; Ile; Val; Nva; NMeAla; NMeAbu; NMeLeu; NMeIle; NMeVal; Tyr; Phe; Trp; Dab; Dap; Orn; or Lys.

In another further particular embodiment of the invention the elements of general formula (I) are defined as follows
T¹ is ᴰPro; or ᴰAzt;
T² is Pro; Ala; Leu; NMeAla; Tyr; Phe; Dab; Dap; Orn; or Lys;
P¹ is Leu; Ile; Val; Nle; Phe; or Trp;
P² is Tyr; Dab; Dap; or Lys;
P³ is Val; tBuGly; or Tyr;
P⁴ is Ala; Val; Dab; Arg; Asn; or Thr;
P⁵ is Orn; Dap; Dab; or Thr;
P⁶ is Gly; Dab; or ᴰDab;
P⁷ is Dab;
P⁸ is Trp; Phe; or Leu;
P⁹ is Ala; Tyr; Dab; Dap; Ser; or Thr;
P¹⁰ is Val; tBuGly; Chg; Phg; or Tyr;
P¹¹ is Ala; Val; Ser; Thr; Asp; Glu; Dap; Dab; or Lys;
P¹² is Val; Tyr; His; Dab; Ser; or Thr;
or a pharmaceutically acceptable salt thereof;
with the proviso that
if T¹ is ᴰPro;
then
T² is Ala; Leu; NMeAla; Tyr; Phe; Dab; Dap; Orn; or Lys.

In another further particular embodiment of the invention the elements of general formula (I) are defined as follows
T¹ is ᴰPro; or ᴰAzt;
T² is Pro; Leu; Tyr; or Phe;
P¹ is Val; or Phe;
P² is Dap;
P³ is Tyr;
P⁴ is Dab;
P⁵ is Orn; or Dap;
P⁶ is ᴰDab;
P⁷ is Dab;
P⁸ is Trp;
P⁹ is Dab;
P¹⁰ is tBuGly;
P¹¹ is Ala; or Ser;
P¹² is Ser; or Thr;
or a pharmaceutically acceptable salt thereof;
with the proviso that
if T¹ is ᴰPro;
then
T² is Leu; Tyr; or Phe.

In another further particular embodiment of the invention the elements of general formula (I) are defined as follows
T¹ is ᴰPro; ᴰAzt; or ᴰTic;
T² is Dab; Dap; Orn; or Lys;
P¹ is Ala; Abu; Leu; Ile; Val; Nva; Nle; Cpa; Cpg; Phe; Tyr; or Trp;
P² is Tyr; Phe; or Trp;
P³ is Val; tBuGly; Ala; Leu; Ile; Val; Nva; Tyr; Phe; or Trp;
P⁴ is Ala; Val; Abu; Leu; Ile; Nva; Asn; Gln; Thr; alloThr; Ser; or Hse;
P⁵ is Orn; Dap; Dab; Lys; or Arg;
P⁶ is Dab; ᴰDab; Dap; ᴰDap; Orn; ᴰOrn; Lys; ᴰLys; Arg; or ᴰArg;

P⁷ is Dab; Dap; Orn; Lys; or Arg;
P⁸ is Trp; Phe; Tyr; Phg; Leu; Ile; Val; Nva; Abu; or Ala;
P⁹ is Ala; Abu; Leu; Ile; Val; Nva; Tyr; Phe; Trp; Ser; Thr; alloThr; or Hse;
P¹⁰ is Val; tBuGly; Ala; Leu; Ile; Nva; Abu; Chg; Phg; Tyr; Phe; or Trp;
P¹¹ is Ala; Val; Abu; Nva; Leu; Ile; Ser; Thr; alloThr; Hse; Asn; Gln; Asp; or Glu;
P¹² is Val; Ala; Abu; Nva; Leu; Ile; Tyr; His; Phe; Trp; Ser; Thr; alloThr; or Hse;
P² and P¹¹ taken together and/or P⁴ and P⁹ taken together form interstrand linking bis(amino acid)-structures based on the linkage of two L- or D-amino acid residues following
connection of the side chain of Cys; or Hcy; with the side chain of Cys; or Hcy; by a disulfide linkage; or
connection of the side chain of Dap; Dab; Orn; or Lys; with the side chain of Asp; Glu; or hGlu; by a lactam linkage; or
connection of the side chain of Dap; Dab; or Orn; with the side chain of Dap; Dab; or Orn; by an urea linkage;
or a pharmaceutically acceptable salt thereof.

In another further particular embodiment of the invention the elements of general formula (I) are defined as follows
T¹ is ᴰPro; or ᴰAzt;
T² is Dab; Dap; Orn; or Lys;
P¹ is Leu; Ile; Val; Cpa; Cpg; Phe; or Trp;
P² is Tyr;
P³ is Val; tBuGly; or Tyr;
P⁴ is Ala; Val; Asn; or Thr;
P⁵ is Orn; Dap; or Dab;
P⁶ is Dab; or ᴰDab;
P⁷ is Dab;
P⁸ is Trp; Phe; or Leu;
P⁹ is Ala; Tyr; Ser; or Thr;
P¹⁰ is Val; tBuGly; Chg; Phg; or Tyr;
P¹¹ is Ala; Val; Ser; Thr; Asp; or Glu;
P¹² is Val; Tyr; His; Ser; or Thr;
P² and P¹¹ taken together and/or P⁴ and P⁹ taken together form interstrand linking bis(amino acid)-structures based on the linkage of two L- or D-amino acid residues following
connection of the side chain of Cys; or Hcy; with the side chain of Cys; or Hcy; by a disulfide linkage; or
connection of the side chain of Dap; Dab; or Lys; with the side chain of Asp; or Glu; by a lactam linkage; or
connection of the side chain of Dap; or Dab; with the side chain of Dap; or Dab; by an urea linkage;
or a pharmaceutically acceptable salt thereof.

In another further particular embodiment of the invention the elements of general formula (I) are defined as follows
T¹ is ᴰPro;
T² is Dab; Dap; Orn; or Lys;
P¹ is Leu;
P³ is Tyr;
P⁴ is Ala;
P⁵ is Orn; or Dab;
P⁶ is Dab; or ᴰDab;
P⁷ is Dab;
P⁸ is Trp;
P⁹ is Ala;
P¹⁰ is Val;
P¹² is Val;
P² and P¹ taken together form interstrand linking bis(amino acid)-structures based on the linkage of two L- or D-amino acid residues following connection of the side chain of Cys; with the side chain of Cys; by a disulfide linkage;

or a pharmaceutically acceptable salt thereof.

Hereinafter follows a list of abbreviations, corresponding to generally adopted usual practice, of amino acids which, or the residues of which, are suitable for the purposes of the present invention and referred to in this document.

In spite of this specific determination of amino acids, it is noted that, for a person skilled in the art, it is obvious that derivatives of these amino acids, resembling alike structural and physico-chemical properties, lead to functional analogs with similar biological activity, and therefore still form part of the gist of this invention.

Ala L-Alanine
Arg L-Arginine
Asn L-Asparagine
Asp L-Aspartic acid
Cit L-Citrulline
Cys L-Cysteine
Gln L-Glutamine
Glu L-Glutamic acid
Gly Glycine
His L-Histidine
Ile L-Isoleucine
Leu L-Leucine
Lys L-Lysine
Met L-Methionine
Orn L-Ornithine
Phe L-Phenylalanine
Pro L-Proline
Ser L-Serine
Thr L-Threonine
Trp L-Tryptophan
Tyr L-Tyrosine
Val L-Valine
Abu (S)-2-aminobutanoic acid
Agp (S)-2-amino-3-guanidinopropanoic acid
Ala(tBu) (S)-2-amino-4,4-dimethylpentanoic acid
Ala(4butoxyPhUr) (S)-2-amino-3-(3-(4-butoxyphenyl)ureido)propanoic acid
Ala(cHex) (S)-2-amino-3-cyclohexylpropanoic acid
Ala(cPr) (S)-2-amino-3-cyclopropylpropanoic acid
Ala(iPrUr) (S)-2-amino-3-(3-isopropylureido)propanoic acid
Ala(2ClPhUr) (S)-2-amino-3-(3-(2-chlorophenyl)ureido)propanoic acid
Ala(4ClPhUr) (S)-2-amino-3-(3-(4-chlorophenyl)ureido)propanoic acid
Ala(2Furyl) (S)-2-amino-3-(furan-2-yl)propanoic acid
Ala(3Furyl) (S)-2-amino-3-(furan-3-yl)propanoic acid
Ala(1Im) (S)-2-amino-3-(1H-imidazol-1-yl)propanoic acid
Ala(2Im) (S)-2-amino-3-(1H-imidazol-2-yl)propanoic acid
Ala(Ppz) (S)-2-amino-3-(piperazin-1-yl)propanoic acid
Ala(cPr) (S)-2-amino-3-cyclopropylpropanoic acid
Ala(Pyrazinyl) (S)-2-amino-3-(pyrazin-2-yl)propanoic acid
Ala(1Pyrazolyl) (S)-2-amino-3-(1H-pyrazol-1-yl)propanoic acid
Ala(3Pyrazolyl) (S)-2-amino-3-(1H-pyrazol-3-yl)propanoic acid
Ala(2Pyrimidin) (S)-2-amino-3-(pyrimidin-2-yl)propanoic acid
Ala(4Pyrimidin) (S)-2-amino-3-(pyrimidin-4-yl)propanoic acid
Ala(5Pyrimidin) (S)-2-amino-3-(pyrimidin-5-yl)propanoic acid
Ala(3PyrMeUr) (S)-2-amino-3-(3-(pyridin-3-ylmethyl)ureido)propanoic acid
Ala(2Quin) (S)-2-amino-3-(quinolin-2-yl)propanoic acid
Ala(3Quin) (S)-2-amino-3-(quinolin-3-yl)propanoic acid
Ala(4Quin) (S)-2-amino-3-(quinolin-4-yl)propanoic acid
Alb (S)-2-amino-3-ureidopropanoic acid
tBuGly (S)-2-amino-3,3-dimethylbutanoic acid
Bbta (S)-2-amino-3-(1-benzothiophen-3-yl)propanoic acid
Bip (S)-2-amino-3-(4-biphenylyl)propanoic acid
Cha (S)-2-amino-3-cyclohexylpropanoic acid
Chg (S)-2-amino-2-cyclohexylacetic acid
Cpa (S)-2-amino-3-cyclopentylpropanoic acid
Cpg (S)-2-amino-2-cyclopentylacetic acid
Dab (S)-2,4-diaminobutanoic acid
Dab(Ac) (S)-4-acetamido-2-aminobutanoic acid
Dab(cPr) (S)-2-amino-4-(cyclopropylamino)butanoic acid
Dab(iPr) (S)-2-amino-4-(isopropylamino)butanoic acid
Dab(2PyrMe) (S)-2-amino-4-(pyridin-2-ylmethylamino)butanoic acid
Dap (S)-2,3-diaminopropanoic acid
Dap(Ac) (S)-3-acetamido-2-aminopropanoic acid
Dap(AcThr) (S)-3-((2S,3R)-2-acetamido-3-hydroxybutanamido)-2-aminopropanoic acid
Dap(cPr) (S)-2-amino-3-(cyclopropylamino)propanoic acid
Dap(iPr) (S)-2-amino-3-(isopropylamino)propanoic acid
Dap(MeSO$_2$) (S)-2-amino-3-(methylsulfonamido)propanoic acid
Dap(2,3-OHpropionyl) (2S)-2-amino-3-(2,3-dihydroxypropanamido)propanoic acid
Dap(Thr) (S)-2-amino-3-((2S,3R)-2-amino-3-hydroxybutanamido)-propanoic acid
Gly(cPr) (S)-2-amino-2-cyclopropylacetic acid
hAla(1Im) (S)-2-amino-3-(1H-imidazol-1-yl)-butanoic acid
hAla(2Im) (S)-2-amino-3-(1H-imidazol-2-yl)-butanoic acid
hArg (S)-2-amino-6-guanidinohexanoic acid
hCha (S)-2-amino-4-cyclohexylbutanoic acid
hCys, hCy (S)-2-amino-4-mercaptobutanoic acid
hHis (S)-2-amino-4-(1H-imidazol-5-yl)butanoic acid
hLeu (S)-2-amino-5-methylhexanoic acid
hLys (S)-2,7-diaminoheptanoic acid
h2Pal (S)-2-amino-4-(pyridin-2-yl)-butanoic acid
h3Pal (S)-2-amino-4-(pyridine-3-yl)-butanoic acid
h4Pal (S)-2-amino-4-(pyridine-4-yl)-butanoic acid
hSer, Hse (S)-2-amino-4-hydroxybutanoic acid
hTrp (S)-2-amino-4-(1H-indol-3-yl)butanoic acid
hTyr (S)-2-amino-4-(4-hydroxyphenyl)butanoic acid
His(Me) (S)-2-amino-3-(1-methyl-1H-imidazol-5-yl)propanoic acid
His(Bn) (S)-2-amino-3-(1-benzyl-1H-imidazol-5-yl)propanoic acid
Lys(Bz) (S)-2-amino-6-benzamidohexanoic acid
Lys(Me) (S)-2-amino-6-(methylamino)hexanoic acid
Lys(Nic) (S)-2-amino-6-(nicotinamido)hexanoic acid
Met(O$_2$) (S)-2-amino-4-(methylsulfonyl)butanoic acid
1Nal (S)-2-amino-3-naphthalen-1-ylpropanoic acid
2Nal (S)-2-amino-3-naphthalen-2-ylpropanoic acid
Nle (S)-2-amino-hexanoic acid
Nle(6OBn) (S)-2-amino-6-(benzyloxy)hexanoic acid
NMeGly N-Methylglycine
NMeAla L-N-Methylalanine
NMeAbu N-Methyl-(S)-2-aminobutanoic acid
NMeVal L-N-Methylvaline
NMeLeu L-N-Methylleucine
NMeIle L-N-Methylisoleucine
Nva (S)-2-aminopentanoic acid
OctG (S)-2-aminodecanoic acid
Oic (2S,3aS,7aS)-octahydro-1H-indole-2-carboxylic acid
Orn(Ac) (S)-5-acetamido-2-aminopentanoic acid
Orn(cPr) (S)-2-amino-5-(cyclopropylamino)pentanoic acid Orn(iPr) (S)-2-amino-5-(isopropylamino)pentanoic acid
2Pal (S)-2-amino-3-(pyridine-2-yl) propionic acid
3Pal (S)-2-amino-3-(pyridine-3-yl)propionic acid
4Pal (S)-2-amino-3-(pyridine-4-yl)propionic acid
Phe(2Cl) (S)-2-amino-3-(2-chlorophenyl)propanoic acid
Phe(3Cl) (S)-2-amino-3-(3-chlorophenyl)propanoic acid
Phe(4Cl) (S)-2-amino-3-(4-chlorophenyl)propanoic acid
Phe(3,4Cl$_2$) (S)-2-amino-3-(3,4-dichlorophenyl)propanoic acid
Phe(2F) (S)-2-amino-3-(2-fluorophenyl)propanoic acid
Phe(3F) (S)-2-amino-3-(3-fluorophenyl)propanoic acid
Phe(4F) (S)-2-amino-3-(4-fluorophenyl)propanoic acid
Phe(3,4F$_2$) (S)-2-amino-3-(3,4-difluorophenyl)propanoic acid
Phe(3CN) (S)-2-amino-3-(3-cyanophenyl)propanoic acid
Phe(4CN) (S)-2-amino-3-(4-cyanophenyl)propanoic acid
Phe(2CF$_3$) (S)-2-amino-3-(2-(trifluoromethyl)phenyl)propanoic acid
Phe(3CF$_3$) (S)-2-amino-3-(3-(trifluoromethyl)phenyl)propanoic acid
Phe(4CF$_3$) (S)-2-amino-3-(4-(trifluoromethyl)phenyl)propanoic acid
Phe(3,4(CF$_3$)$_2$) (S)-2-amino-3-(3,4-bis(trifluoromethyl)phenyl)propanoic acid
Phe(4COOMe) (S)-2-amino-3-(4-(methoxycarbonyl)phenyl)propanoic acid
Phe(4NH$_2$) (S)-2-amino-3-(4-aminophenyl)propanoic acid
Phe(3OH) (S)-2-amino-3-(3-hydroxyphenyl)propanoic acid
Phg (S)-2-amino-2-phenylacetic acid
Pic (S)-piperidine-2-carboxylic acid
Pip 4-aminopiperidine-4-carboxylic acid
Pro((4R)NH$_2$) (2S,4R)-4-aminopyrrolidine-2-carboxylic acid
Pro((4S)NH$_2$) (2S,4S)-4-aminopyrrolidine-2-carboxylic acid
Pro((3R)OH) (2S,3R)-3-hydroxypyrrolidine-2-carboxylic acid
Pro((3S)OH) (2S,3S)-3-hydroxypyrrolidine-2-carboxylic acid
Pro((4R)OH) (2S,4R)-4-hydroxypyrrolidine-2-carboxylic acid
Pro((4S)OH) (2S,4S)-4-hydroxypyrrolidine-2-carboxylic acid
Pro((4R)OBn) (2S,4R)-4-(benzyloxy)pyrrolidine-2-carboxylic acid
Pro((4S)OBn) (2S,4S)-4-(benzyloxy)pyrrolidine-2-carboxylic acid
Sar; NMeGly N-Methylglycine
Ser(Bn) (S)-2-amino-3-(benzyloxy)propanoic acid
Ser(Me) (S)-2-amino-3-methoxy-propanoic acid
Thi (S)-2-amino-3-(thiophen-2-yl)propanoic acid
alloThr (2S,3S)-2-amino-3-hydroxybutanoic acid
Thr(Bn) (2S,3R)-2-amino-3-(benzyloxy)butanoic acid
Thr(Me) (2S,3R)-2-amino-3-(methyloxy)butanoic acid
Thz (R)-thiazolidine-4-carboxylic acid
Thz(5,5Me$_2$) (R)-2,2-dimethylthiazolidine-4-carboxylic acid
Tic (S)-1,2,3,4-Tetrahydroisoquinoline-3-carboxylic acid
Tic(7OH) (S)-7-hydroxy-1,2,3,4-tetrahydroisoquinoline-3-carboxylic acid
Trp(7Aza) (S)-2-amino-3-(1H-pyrrolo[2,3-b]pyridin-3-yl)propanoic acid
Trp(5Br) (S)-2-amino-3-(5-bromo-1H-indol-3-yl)propanoic acid
Trp(6Br) (S)-2-amino-3-(6-bromo-1H-indol-3-yl)propanoic acid
Trp(6CF$_3$) (S)-2-amino-3-(6-(trifluoromethyl)-1H-indol-3-yl)propanoic acid
Trp(5Cl) (S)-2-amino-3-(5-chloro-1H-indol-3-yl)propanoic acid
Trp(6Cl) (S)-2-amino-3-(6-chloro-1H-indol-3-yl)propanoic acid
Trp(5,6Cl) (S)-2-amino-3-(5,6-dichloro-1H-indol-3-yl)propanoic acid
Trp(5OH) (S)-2-amino-3-(5-hydroxy-1H-indol-3-yl)propanoic acid
Tyr(Bn) (S)-2-amino-3-(4-(benzyloxy)phenyl)propanoic acid
Tyr(Me) (S)-2-amino-3-(4-methoxyphenyl)propanoic acid
Tyr(Ph) (S)-2-amino-3-(4-phenoxyphenyl)propanoic acid
Tyr(4OHPh) (S)-2-amino-3-[4-(4-hydroxyphenoxy)phenyl]propanoic acid
Tyr(3F) (S)-2-amino-3-(3-fluoro-4-hydroxyphenyl)propanoic acid
Tza (S)-2-amino-3-(thiazol-4-yl)propanoic acid The abbreviation of D-isomers, e.g. $^D$Lys corresponds to the epimer at the 2-position of the appropriate amino acid described above. Same applies for the generic descriptions of the amino acids, e.g. AA1 which has AA1$^D$ as the corresponding α-epimer.

In a preferred embodiment of the invention the β-hairpin peptidomimetics are selected from a group consisting of β-hairpin peptidomimetics of general formula (I) having a disulfide linkage; a lactam linkage; or a urea linkage between P$^2$ and P$^{11}$:

cyclo(-Leu-Cys-Tyr-Ala-Dab-Dab-Dab-Trp-Ala-Val-Cys-Val-$^D$Pro-Dab-);
cyclo(-Leu-Cys-Tyr-Ala-Dab-$^D$Dab-Dab-Trp-Ala-Val-Cys-Val-$^D$Pro-Dab-);
cyclo(-Leu-Cys-Tyr-Ala-Orn-$^D$Dab-Dab-Trp-Ala-Val-Cys-Val-$^D$Pro-Lys-);
cyclo(-Leu-Cys-Tyr-Ala-Orn-$^D$Dab-Dab-Trp-Ala-Val-Cys-Val-$^D$Pro-Orn-);
cyclo(-Leu-Cys-Tyr-Ala-Orn-$^D$Dab-Dab-Trp-Ala-Val-Cys-Val-$^D$Pro-Dab-);
cyclo(-Leu-Cys-Tyr-Ala-Orn-$^D$Dab-Dab-Trp-Ala-Val-Cys-Val-$^D$Pro-Dap-);
cyclo(-Ile-Cys-Tyr-Dab-Orn-$^D$Dab-Dab-Leu-Dab-Val-Cys-Tyr-$^D$Pro-Pro-);
cyclo(-Val-Cys-Tyr-Dab-Dap-Dab-Dab-Trp-Dab-tBuGly-Cys-Thr-$^D$Pro-Pro-);
cyclo(-Val-Cys-Tyr-Dab-Dap-$^D$Dab-Dab-Trp-Dab-tBuGly-Cys-Ser-$^D$Pro-NMeAla-);
cyclo(-Ile-Cys-Tyr-Dab-Orn-$^D$Dab-Dab-Trp-Dab-tBuGly-Cys-Ser-$^D$Pro-Pro-);
cyclo(-Ile-Cys-Tyr-Dab-Orn-$^D$Dab-Dab-Trp-Dab-tBuGly-Cys-Ser-$^D$Pro-Tyr-);
cyclo(-Val-Dab-Tyr-Dab-Dap-$^D$Dab-Dab-Trp-Dab-tBuGly-Asp-Thr-$^D$Azt-Pro-);
cyclo(-Phe-Dab-Tyr-Arg-Orn-$^D$Dab-Dab-Trp-Dab-tBuGly-Asp-Ser-$^D$Pro-Pro-);
cyclo(-Trp-Dab-Tyr-Dab-Dab-$^D$Dab-Dab-Trp-Dab-tBuGly-Asp-Ser-$^D$Pro-Pro-);
cyclo(-Trp-Dab-Tyr-Dab-Dab-Dab-Dab-Trp-Dab-tBuGly-Asp-Ser-$^D$Azt-Pro-);
cyclo(-Val-Dab-Tyr-Dab-Dab-$^D$Dab-Dab-Trp-Dab-Phg-Asp-Ser-$^D$Pro-Pro-);
cyclo(-Val-Dab-Tyr-Dab-Thr-Dab-Dab-Trp-Dab-tBuGly-Asp-His-$^D$Pro-Pro-);
cyclo(-Leu-Glu-Tyr-Dab-Orn-Dab-Dab-Trp-Dab-tBuGly-Dap-$^D$Pro-Pro-);
cyclo(-Leu-Glu-Tyr-Dab-Orn-$^D$Dab-Dab-Trp-Dab-tBuGly-Dab-Ser-$^D$Pro-Pro-);

cyclo(-Leu-Glu-Tyr-Dab-Orn-$^D$Dab-Dab-Trp-Dab-tBuGly-Lys-Ser-$^D$Pro-Pro-);
cyclo(-Leu-Asp-Tyr-Dab-Orn-$^D$Dab-Dab-Trp-Dab-tBuGly-Dap-Ser-$^D$Pro-Pro-);
cyclo(-Leu-Asp-Tyr-Dab-Orn-$^D$Dab-Dab-Trp-Dab-tBuGly-Dab-Ser-$^D$Pro-Pro-);
cyclo(-Leu-Asp-Tyr-Dab-Orn-Dab-Dab-Trp-Dab-tBuGly-Dab-Ser-$^D$Pro-Pro-);
cyclo(-Leu-Asp-Tyr-Dab-Orn-$^D$Dab-Dab-Trp-Dab-tBuGly-Lys-Ser-$^D$Pro-Pro-);
cyclo(-Leu-Asp-Tyr-Dab-Orn-Dab-Dab-Trp-Dab-tBuGly-Lys-Ser-$^D$Pro-Pro-);
cyclo(-Leu-Dap-Tyr-Dab-Orn-Dab-Dab-Trp-Dab-tBuGly-Glu-Ser-$^D$Pro-Pro-);
cyclo(-Leu-Lys-Tyr-Dab-Orn-$^D$Dab-Dab-Trp-Dab-tBuGly-Glu-Ser-$^D$Pro-Pro-);
cyclo(-Val-Dap-Tyr-Dab-Dab-$^D$Dab-Dab-Trp-Dab-tBuGly-Asp-Ser-$^D$Pro-Pro-);
cyclo(-Leu-Dap-Tyr-Dab-Orn-$^D$Dab-Dab-Trp-Dab-tBuGly-Glu-Ser-$^D$Pro-Pro-);
cyclo(-Leu-Dab-Tyr-Dab-Orn-$^D$Dab-Dab-Trp-Dab-tBuGly-Glu-Ser-$^D$Pro-Pro-);
cyclo(-Leu-Dap-Tyr-Dab-Orn-Dab-Dab-Trp-Dab-tBuGly-Asp-Ser-$^D$Pro-Pro-);
cyclo(-Leu-Dab-Tyr-Dab-Orn-Dab-Dab-Trp-Dab-tBuGly-Asp-Ser-$^D$Pro-Pro-);
cyclo(-Leu-Lys-Tyr-Dab-Orn-Dab-Dab-Trp-Dab-tBuGly-Asp-Ser-$^D$Pro-Pro-);
cyclo(-Leu-Glu-Tyr-Dab-Orn-$^D$Dab-Dab-Trp-Dab-tBuGly-Dap-Ser-$^D$Pro-Pro-);
cyclo(-Leu-Lys-Tyr-Dab-Orn-$^D$Dab-Dab-Trp-Dab-tBuGly-Asp-Ser-$^D$Pro-Pro-);
cyclo(-Leu-Dap-Tyr-Dab-Orn-$^D$Dab-Dab-Trp-Dab-tBuGly-Asp-Ser-$^D$Pro-Pro-);
cyclo(-Leu-Dab-Tyr-Dab-Orn-$^D$Dab-Dab-Trp-Dab-tBuGly-Asp-Ser-$^D$Pro-Pro-);
cyclo(-Val-$^D$Cys-Tyr-Dab-Dap-$^D$Dab-Dab-Trp-Dab-tBu-Gly-$^D$Cys-Ser-$^D$Pro-Pro-);
cyclo(-Val-Hcy-Tyr-Dab-Dap-$^D$Dab-Dab-Trp-Dab-tBuGly-Cys-Ser-$^D$Pro-Pro-);
cyclo(-Val-Dap-Tyr-Dab-Dap-$^D$Dab-Dab-Trp-Dab-tBuGly-Dap-Ser-$^D$Pro-Pro-);
or a pharmaceutically acceptable salt thereof;
and/or
a group consisting of β-hairpin peptidomimetics of general formula (I)
cyclo(-Val-Dap-Tyr-Dab-Dap-$^D$Dab-Dab-Trp-Dab-tBuGly-Ser-Thr-$^D$Azt-Pro-);
cyclo(-Phe-Dap-Tyr-Dab-Orn-$^D$Dab-Dab-Trp-Dab-tBuGly-Ala-Ser-$^D$Pro-Leu-);
cyclo(-Phe-Dap-Tyr-Dab-Orn-$^D$Dab-Dab-Trp-Dab-tBuGly-Ala-Ser-$^D$Pro-Phe-);
cyclo(-Phe-Dap-Tyr-Dab-Orn-$^D$Dab-Dab-Trp-Dab-tBuGly-Ala-Ser-$^D$Pro-Tyr-);
or a pharmaceutically acceptable salt thereof.

In another preferred embodiment of the invention the β-hairpin peptidomimetics of general formula (I) having a disulfide linkage between $P^2$ and $P^{11}$ are selected from the group consisting of:
cyclo(-Leu-Cys-Tyr-Ala-Dab-Dab-Dab-Trp-Ala-Val-Cys-Val-$^D$Pro-Dab-);
cyclo(-Leu-Cys-Tyr-Ala-Dab-$^D$Dab-Dab-Trp-Ala-Val-Cys-Val-$^D$Pro-Dab-);
cyclo(-Leu-Cys-Tyr-Ala-Orn-Dab-Dab-Trp-Ala-Val-Cys-Val-$^D$Pro-Lys-);
cyclo(-Leu-Cys-Tyr-Ala-Orn-$^D$Dab-Dab-Trp-Ala-Val-Cys-Val-$^D$Pro-Orn-);
cyclo(-Leu-Cys-Tyr-Ala-Orn-$^D$Dab-Dab-Trp-Ala-Val-Cys-Val-$^D$Pro-Dab-);
cyclo(-Leu-Cys-Tyr-Ala-Orn-$^D$Dab-Dab-Trp-Ala-Val-Cys-Val-$^D$Pro-Dap-);
or a pharmaceutically acceptable salt thereof.

In accordance with the present invention these β-hairpin peptidomimetics can be prepared by a process which comprises a) coupling an appropriately functionalized solid support with an appropriately N-protected derivative of that amino acid which in the desired end-product is in position $T^1$ or $T^2$ or $P^1$ to $P^{12}$ as defined above; any functional group which may be present in said N-protected amino acid derivative being likewise appropriately protected;
(b) removing the N-protecting group from the product obtained in step (a);
(c) coupling the product thus obtained with an appropriately N-protected derivative of that amino acid which in the desired end-product is in the position of the next element (T or P), following counterclockwise or clockwise the sequence according to general formula (I) in —COOH to —NH2 orientation; any functional group which may be present in said N-protected amino acid derivative being likewise appropriately protected;
(d) removing the N-protecting group from the product thus obtained;
(e) repeating steps (c) and (d) until all amino acid residues have been introduced;
(f) if desired, selectively deprotecting one or several protected functional group(s) present in the molecule and chemically transforming the reactive group(s) thus liberated;
(g) detaching the product thus obtained from the solid support;
(h) cyclizing the product cleaved from the solid support;
(i) if desired, selectively deprotecting one or several protected functional group(s) present in the molecule and chemically transforming the reactive group(s) thus liberated;
(j) removing any protecting groups present on functional groups of any members of the chain of amino acid residues and, if desired, any protecting group(s) which may in addition be present in the molecule;
(k) if desired, implementing additional chemical transformations of one or more reactive group(s) present in the molecule; and
(l) if required, removing any protecting groups present on functional groups of any members of the chain of amino acid residues and, if desired, any protecting group(s) which may in addition be present in the molecule;
(m) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

Enantiomers of the compounds defined herein before form also part of the present invention. These enantiomers can be prepared by a modification of the above process wherein enantiomers of all chiral starting materials are utilized.

The process of the invention can advantageously be carried out as parallel array synthesis to yield libraries of β-hairpin peptidomimetics of the invention. Such parallel syntheses allow one to obtain arrays of numerous (normally 12 to 576, typically 96) compounds as described above in moderate to high yields and defined purities, minimizing the formation of dimeric and polymeric by-products. The proper choice of the functionalized solid-support (i.e. solid support plus linker molecule) and site of cyclization play thereby key roles.

The functionalized solid support is conveniently derived from polystyrene crosslinked with, preferably 1-5%, divinylbenzene; polystyrene coated with polyethyleneglycol spacers (Tentagel™); and polyacrylamide resins (see also D. Obrecht, J.-M. Villalgordo, "Solid-Supported Combinatorial and Parallel Synthesis of Small-Molecular-Weight Compound Libraries", Tetrahedron Organic Chemistry Series, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (H. Rink, Tetrahedron Lett. 1987, 28, 3783-3790). Linkers of this kind form amides of the carboxyl group of the amino acids; examples of resins functionalized by such linker structures include 4-[(((2,4-dimethoxyphenyl)Fmoc-aminomethyl) phenoxyacetamido) aminomethyl] PS resin, 4-[(((2,4-dimethoxyphenyl) Fmoc-aminomethyl)phenoxyacetamido) aminomethyl]-4-methylbenzydrylamine PS resin (Rink amide MBHA PS Resin), and 4-[(((2,4-dimethoxy-phenyl) Fmoc-aminomethyl)phenoxyacetamido) aminomethyl] benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxy-phenyl) Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin™ linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array synthesis the process of the invention can be advantageously carried out as described herein below but it will be immediately apparent to those skilled in the art how these procedures will have to be modified in case it is desired to synthesize one single compound of the invention.

A number of reaction vessels (normally 12 to 576, typically 96) equal to the total number of compounds to be synthesized by the parallel method are loaded with 25 to 1000 mg, preferably 60 mg, of the appropriate functionalized solid support, preferably 1 to 5% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (G. B. Fields, C. G. Fields, J. Am. Chem. Soc. 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin™ linker, Mergler et al., Tetrahedron Lett. 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2, 4-dimethoxyphenyl-hydroxymethyl)-phenoxy linker (Rink linker, H. Rink, Tetrahedron Lett. 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, 1991, Peptides 1990: Proceedings of the Twenty-First European Peptide Symposium, 131) which is also cleaved with 1% TFA/DCM in order to yield a peptide fragment containing all acid labile side-chain protective groups; and, in addition, the 2-chlorotritylchloride linker (Barlos et al., Tetrahedron Lett. 1989, 30, 3943-3946), which allows the peptide detachment using a mixture of glacial acetic acid/trifluoroethanol/ DCM (1:2:7) for 30 min.

Suitable protecting groups for amino acids and, respectively, for their residues are, for example, for the amino group (as is present e.g. also in the side-chain of lysine)

Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl
Trt triphenylmethyl or trityl
ivDe 1-(4,4-dimethyl-2,6-dioxocyclohex-1-ylidene)-3-methylbutyl;

for the carboxyl group (as is present e.g. also in the side-chain of aspartic and glutamic acid) by conversion into esters with the alcohol components tBu tert.-butyl
Bn benzyl
Me methyl
Ph phenyl
Pac phenacyl
allyl
Tse trimethylsilylethyl
Tce trichloroethyl
Dmab 4-N-(1-[dimethyl-2,6-dioxocyclohexylidene]-3-methylbutyl)-amino benzyl;

for the guanidino group (as is present e.g. in the side-chain of arginine)

Pmc 2,2,5,7,8-pentamethylchroman-6-sulfonyl
Ts tosyl (i.e. p-toluenesulfonyl)
Cbz benzyloxycarbonyl
Pbf pentamethyldihydrobenzofuran-5-sulfonyl;

and for the hydroxy group (as is present e.g. in the side-chain of threonine and serine)

tBu tert.-butyl
Bn benzyl
Trt trityl
Alloc allyloxycarbonyl.

The 9-fluorenylmethoxycarbonyl-(Fmoc)-protected amino acid derivatives are preferably used as the building blocks for the construction of the β-hairpin loop mimetics of the invention. For the deprotection, i.e. cleaving off of the Fmoc group, 20% piperidine in DMF or 2% DBU/2% piperidine in DMF can be used as well as 25% hexafluoroisopropanol in $CH_2Cl_2$.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and, respectively, diisopropylurea is insoluble and, respectively, soluble in the solvents generally used. In a variation of the carbodiimide method 1-hydroxy benzotriazole (HOBt, König & Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethyl-amino)-phosphonium hexafluorophosphate (BOP, Castro et al., *Tetrahedron Lett.* 1975, 14, 1219-1222; *Synthesis* 1976, 751-752), or benzotriazol-1-yl-oxy-tris-pyrrolidino-phosphonium hexaflurophoshate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoro borate (TATU) or O-(7-aza-benzotriazol-1-yl)-N,N,N',N'-tetramethyluronium hexafluorophosphate (HATU)/7-aza-1-hydroxybenzotriazole (HOAt, Carpino et al., *Tetrahedron Lett.* 1994, 35, 2279-2281) or -(6-Chloro-1H-benzotriazol-1-yl-)-N,N,N',N'-1,1,3,3-tetramethyl uronium tetrafluoroborate (TCTU), or hexafluoro phosphate (HCTU, Marder, Shivo and Albericio: HCTU and TCTU: New Coupling Reagents: Development and Industrial Applications, Poster Presentation, Gordon Conference February 2002) have also been used as coupling reagents as well as 1,1,3,3-bis(tetramethylene)chlorouronium hexafluorophosphate (PyCIU) especially for coupling of N-methylated amino acids (J. Coste, E. Frérot, P. Jouin, B. Castro, *Tetrahedron Lett.* 1991, 32, 1967) or pentafluorophenyl diphenyl-phosphinate (S. Chen, J. Xu, *Tetrahedron Lett.* 1991, 32, 6711).

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide or peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction vessel is washed free of excess of retained reagents, of solvents, and of by-products by repetitive exposure to pure solvent(s).

Washing procedures are repeated up to about 30 times (preferably about 5 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

After detachment of the fully protected linear peptide from the solid support the individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier as activators for the amide bond formation can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS, or 87.5% TFA, 2.5% DODT, 5% thioanisol, 5% $H_2O$ or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefore. The aqueous layer is collected and evaporated to dryness, and the fully deprotected cyclic peptide is obtained. Alternatively the deprotected cyclic peptide can be precipitated and washed using cold $Et_2O$.

For some compounds of the present invention according general formula (I) additional synthetic steps are required. These transformations can be applied either on a fully protected or partially deprotected linear or cyclic peptide, attached to or already released from the solid support or on the final deprotected molecule.

Various methods are known how to form interstrand linkages including those described by: J. P. Tam et al., *Synthesis* 1979, 955-957; J. M. Stewart et al., *Solid Phase Peptide Synthesis*, 2d Ed., Pierce Chemical Company, Rockford, Ill., 1984; A. K. Ahmed et al., *J. Biol. Chem.* 1975, 250, 8477-8482; and M. W. Pennington et al., *Peptides*, pages 164-166, Giralt and Andreu, Eds., ESCOM Leiden, The Netherlands, 1990; C. E. Schafmeister et al., *J. Am. Chem. Soc.* 2000, 122, 5891. The most widely known linkage is the disulfide bridge formed by e.g. cysteines and homo-cysteines positioned at opposite positions of the β-strand.

For instance, the formation of a disulfide bridge can be carried out after assembly of the linear peptide on resin by employing, for example, on trityl protected cysteine amino acid residues, 10 eq of iodine solution in DMF for 1.5 h and repetition of the oxidation step with a fresh iodine solution for additional 3 h. Alternatively, disulfide bridge formation can be performed in solution after backbone cyclization but before deprotection of the peptide by employing, for example, on trityl protected cysteine amino acid residues, 2 eq of an iodine solution in a hexafluoroisopropanol/$CH_2Cl_2$-mixture for 1 h followed by addition of 1M aqueous solution of ascorbic acid to quench the oxidation reaction. Another possibility to form disulfide bridges remains after deprotection of the backbone-cyclized peptide by, for example, the application of a mixture of DMSO and acetic acid solution, buffered with 5% $NaHCO_3$ to pH 5-6 for 4 h, or in water after adjusting to pH 8 with ammonium hydroxide solution by stirring for 24 h.

Another well established interstrand linkage is the lactam bridge formed by linking e.g. the amino group-bearing side chains of ornithine and lysine, respectively, with the carboxyl group-bearing side chains of glutamic and aspartic acid residues located at opposite β-strand positions by means of an amide bond formation. Preferred protective groups for the side chain amino-groups of ornithine and lysine are allyloxycarbonyl (alloc) and for the side chain carboxyl-groups of aspartic and glutamic acid allylesters (allyl).

For instance, the formation of a lactam bridge can be carried out after assembly of the linear peptide on resin by applying 0.2 eq tetrakis(triphenyl-phosphine)palladium(0) (10 mM) in dry $CH_2Cl_2$ and 10 eq phenylsilane to selectively remove alloc- and allyl-protecting groups from amino and carboxyl functional groups of the side chains of amino acid residues to be linked. After repetition of the above procedure, the lactam bridge is formed by adding 4 eq of DIPEA in DMF and subsequent addition of 2 eq HATU in DMF.

By applying an appropriate orthogonal protecting group strategy lactam bridges may also be formed in a later stage of the synthesis, e.g. after deprotection of backbone cyclized peptides.

Interstrand linkages can also be established by linking side chain amino groups of amino acid residues like e.g. L-1,3-diamino propionic acid and ornithine located at opposite β-strand positions with reagents such as N,N-carbonylimidazole or di(N-succinimidyl)carbonate to form cyclic ureas. Allyloxycarbonyl (alloc) as orthogonal protecting group for amino functions may be preferably used.

For instance, the formation of an urea bridge can be carried out in solution after backbone cyclization, but before full deprotection of the peptide, by applying 30 eq phenylsilane as well as a solution of 0.2 eq tetrakis(triphenylphosphine)-palladium(0) in $CH_2Cl_2$. After removal of the alloc protecting groups and precipitation of the selectively deprotected peptide the urea bridge is formed by adding 6 eq DIPEA dissolved in $CH_2Cl_2$ and subsequent dropwise addition of 1.2 eq of di(N-succinimidyl)carbonate in $CH_2Cl_2$.

Recently, a further type of interstrand linkages based on 1,4-disubstituted 1,2,3-triazole-containing alkanediyl groups have been introduced. The linkage is obtained through a 1,3-dipolar cycloaddition between the ω-yne group of the side chain of an amino acid residue like e.g. L-propargylglycine and the ω-azido group of the side chain of an amino acid residue like e.g. (S)-2-amino-4-azidobutanoic acid, both residues located at opposite β-strand positions.

For instance, the formation of such a triazole-containing bridge is performed by stirring the purified fully deprotected backbone-cyclized peptide in a mixture of $H_2O$/tBuOH, 4.4 eq of $CuSO_4 \times 5H_2O$ and 6.6 eq of ascorbic acid for 12 h.

Depending on its purity, the final product as obtained following the procedures above can be used directly for biological assays, or has to be further purified, for example by preparative HPLC.

As mentioned earlier, it is thereafter possible, if desired, to convert the fully deprotected cyclic product thus obtained into a pharmaceutically acceptable salt or to convert a pharmaceutically acceptable, or unacceptable, salt thus obtained into the corresponding free or into a different, pharmaceutically acceptable, salt. Any of these operations can be carried out by methods well known in the art.

In general the building blocks for the peptidomimetics of the present invention can be synthesized according to the literature methods, which are known to a person skilled in the art or are commercially available. All other corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron* (*Report*) 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989, Chapter 7, p. 257-279). Kinetic resolution using hydrolytic enzymes involves hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron* Report 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989).

The β-hairpin peptidomimetics of the invention can be used in a wide range of applications in order to inhibit the growth of or to kill microorganisms leading to the desired therapeutic effect in man or, due to their similar etiology, in other mammals. In particular they can be used to inhibit the growth of or to kill Gram-negative bacteria such as *Klebsiella pneumoniae* and/or *Acinetobacter baumannii* and/or *Escherichia coli*.

They can be used for example as disinfectants or as preservatives for materials such as foodstuffs, cosmetics, medicaments and other nutrient-containing materials.

The β-hairpin peptidomimetics of the invention can also be used to treat or prevent diseases related to microbial infection in plants and animals.

For use as disinfectants or preservatives the β-hairpin peptidomimetics can be added to the desired material singly, as mixtures of several β-hairpin peptidomimetics or in combination with other antimicrobial agents.

The β-hairpin peptidomimetics of the invention can be used to treat or prevent infections or diseases related to such infections, particularly nosocomial infections caused by Gram-negative bacteria related to diseases such as ventilator-associated pneumonia (VAP), hospital-acquired pneumonia (HAP), healthcare-associated pneumonia (HCAP); catheter-related and non-catheter-related infections such as urinary tract infections (UTIs) or bloodstream infections (BSIs); infections related to respiratory diseases such as cystic fibrosis, emphysema, asthma or pneumonia; infections related to skin or soft tissue diseases such as surgical wounds, traumatic wounds or burn; infections related to gastrointestinal diseases such as epidemic diarrhea, necrotizing enterocolitis, typhlitis, gastroenteritis or pancreatitis; infections related to eye diseases such as keratitis and endophthalmitis; infections related to ear diseases such as otitis; infections related to CNS diseases such as brain abscess and meningitis or encephalitis; infections related to bone diseases such as osteochondritis and osteomyelitis; infections related to cardiovascular diseases such as endocarditis and pericarditis; or infections related to genitourinary diseases such as epididymitis, prostatitis and urethritis. They can be administered singly, as mixtures of several β-hairpin peptidomimetics, in combination with other antimicrobial or antibiotic agents, or anti cancer agents, or antiviral (e.g. anti-HIV) agents, or in combination with other pharmaceutically active agents. The β-hairpin peptidomimetics can be administered per se or as pharmaceutical compositions.

The β-hairpin peptidomimetics of the invention may be administered per se or may be applied as an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aerosol spray from pressurized packs or a nebulizer, with the use of a suitable propellant, e.g. dichlorodifluoromethane, trichlorofluromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described above, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent (e.g. for coated stents). Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The β-hairpin peptidomimetics of the invention, or compositions thereof, will generally be used in an amount effective to achieve the intended purpose. It is to be understood that the amount used will depend on a particular application.

For example, for use as a disinfectant or preservative, an antimicrobially effective amount of a β-hairpin peptidomimetic of the invention, or a composition thereof, is applied or added to the material to be desinfected or preserved. By antimicrobially effective amount is meant an amount of a β-hairpin peptidomimetic of the invention, or a composition thereof, that inhibits the growth of, or is lethal to, a target microbe population. While the antimicrobially effective amount will depend on a particular application, for use as disinfectants or preservatives the β-hairpin peptidomimetics of the invention, or compositions thereof, are usually added or applied to the material to be desinfected or preserved in relatively low amounts. Typically, the β-hairpin peptidomimetics of the invention comprise less than about 5% by weight of a disinfectant solution or material to be preserved, preferably less than 1% by weight and more preferably less than 0.1% by weight. An ordinary skilled expert will be able to determine antimicrobially effective amounts of particular β-hairpin peptidomimetics of the invention for particular applications without undue experimentation using, for example, the results of the in vitro assays provided in the examples.

For use to treat or prevent microbial infections or diseases related to such infections, the β-hairpin peptidomimetics of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the capacities of those skilled in the art, especially in view of the detailed disclosure provided herein. As in the case of disinfectants and preservatives, for topical administration to treat or prevent bacterial infections and/or viral infections a therapeutically effective dose can be determined using, for example, the results of the in vitro assays provided in the examples. The treatment may be applied while the infection is visible, or even when it is not visible. An ordinary skilled expert will be able to determine therapeutically effective amounts to treat topical infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-infective agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The antimicrobial therapy may be repeated intermittently while infections are detectable or even when they are not detectable. The therapy may be provided alone or in combination with other drugs, such as for example anti-HIV agents or anti-cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the present invention but are not to be construed as limiting its scope in any way.

Abbreviations:

Ac Acetyl;
BSA Bovine serum albumin;
Boc tert-Butyloxycarbonyl;
DCHA Dicyclohexylamine;
DEAD Diethyl azodicarboxylate;
DIPEA Diisopropylethylamine;
DMEM Dulbecco's Modified Eagle's Medium;
DODT 3,6-dioxa-1,8-octanedithiol;
FCS Fetal Calf Serum;
Fmoc Fluorenylmethyloxycarbonyl;
HATU O-(7-Aza-benzotriazole-1-yl)-N,N,N',N'-tetramethyluronium hexafluorophosphate;
HBSS Hank's Buffered Salt Solution;
HBTU O-(Benzotriazol-1-yl)-N,N,N',N'-tetramethyluronium hexafluorophosphate;
HCTU O-(6-Chlorobenzotriazol-1-yl)-N,N,N',N'-tetramethyluronium hexafluorophosphate;
Hepes 4-(2-hydroxyethyl)-1-piperazineethanesulfonic acid;
HFIP Hexafluoroisopropanol
HOAt 1-Hydroxy-7-azabenzotriazole;
IMDM Iscove's Modified Dulbecco's Media;
PyBop® (Benzotriazol-1-yloxy)tripyrrolidinophosphonium hexafluorophosphate;
TIS Triisopropylsilane;
TPP Triphenylphosphine;
RPMI Roswell Park Memorial Institute medium;
rt Room temperature.

EXAMPLES

1. Peptide Synthesis

1.1 General Synthetic Procedures

A general method for the synthesis of the peptidomimetics of the present invention is exemplified in the following. This is to demonstrate the principal concept and does not limit or restrict the present invention in any way. A person skilled in the art is easily able to modify these procedures, especially, but not limited to, choosing a different starting position within the ring system, to still achieve the preparation of the claimed cyclic peptidomimetic compounds of the present invention.

Coupling of the First Protected Amino Acid Residue to the Resin

In a dried flask, 2-chlorotritylchloride resin (polystyrene, 1% crosslinked; loading: 1.4 mMol/g) was swollen in dry $CH_2Cl_2$ for 30 min (7 mL $CH_2Cl_2$ per g resin). A solution of 0.8 eq of the Fmoc-protected amino acid and 6 eq of DIPEA in dry $CH_2Cl_2$/DMF (4/1) (10 mL per g resin) was added. After shaking for 2-4 h at rt the resin was filtered off and washed successively with $CH_2Cl_2$, DMF, $CH_2Cl_2$, DMF and $CH_2Cl_2$. Then a solution of dry $CH_2Cl_2$/MeOH/DIPEA (17:2:1) was added (10 mL per g resin). After shaking for 3×30 min the resin was filtered off in a pre-weighed sinter funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

Loading was typically 0.6-0.7 mMol/g.

The following preloaded resins were prepared: Fmoc-Dab (Boc)-2-chlorotrityl resin, Fmoc-$^D$Dab(Boc)-2-chlorotrityl resin, Fmoc-Trp(Boc)-2-chlortrityl resin and Fmoc-Pro-2-chlorotrityl resin.

Synthesis of the Fully Protected Peptide Fragment

The synthesis was carried out on a Syro-peptide synthesizer (MultiSynTech GmbH) using 24 to 96 reaction vessels. In each vessel 0.04 mMol of the above resin were placed and the resin was swelled in $CH_2Cl_2$ and DMF for 15 min, respectively.

The following reaction cycles were programmed and carried out:

| Step | Reagent | Time |
|---|---|---|
| 1 | $CH_2Cl_2$, wash and swell (manual) | 1 × 3 min |
| 2 | DMF, wash and swell | 2 × 30 min |
| 3 | 20% piperidine/DMF | 1 × 5 min and 1 × 15 min |
| 4 | DMF, wash | 5 × 1 min |
| 5 | 3.5 eq Fmoc amino acid/3.5 eq HOAt in DMF + 3.5 eq PyBOP/7 eq DIPEA or 3.5 eq DIC | 1 × 40 min |
| 6 | 3.5 eq Fmoc amino acid/DMF + 3.5 eq HATU or PyBOP or HCTU + 7 eq DIPEA | 1 × 40 min |
| 7 | DMF, wash | 5 × 1 min |
| 8 | 20% piperidine/DMF | 1 × 5 min and 1 × 15 min |
| 9 | DMF, wash | 5 × 1 min |
| 10 | $CH_2Cl_2$, wash (at the end of the synthesis) | 3 × 1 min |

Steps 5 to 9 are repeated to add each amino-acid residue.

After the termination of the synthesis of the fully protected peptide fragment, one of the procedures A-D, as described herein below, was adopted subsequently, depending on which kind of interstrand linkages, as described herein below, were to be formed.

Finally, the peptides were purified by preparative reverse phase LC-MS, as described herein below.

Procedure A: Cyclization and Work Up of a Backbone Cyclized Peptide Having No Interstrand Linkage Cleavage, Backbone Cyclization and Deprotection After assembly of the linear peptide, the resin was suspended in 1 mL of 1% TFA in $CH_2Cl_2$ (v/v; 0.14 mMol) for 3 minutes. After filtration the filtrate was neutralized with 1 mL of 20% DIPEA in $CH_2Cl_2$ (v/v; 1.15 mMol). This procedure was repeated four times to ensure completion of the cleavage. An alternative cleavage method comprises suspension of the resin in 1 mL of 20% HFIP in $CH_2Cl_2$ (v/v; 1.9 mMol) for 30 minutes, filtration and repetition of the procedure. The resin was washed three times with 1 mL of $CH_2Cl_2$. The $CH_2Cl_2$ layers containing product were evaporated to dryness.

The fully protected linear peptide was solubilised in 8 mL of dry DMF. Then 2 eq of HATU and 2 eq of HOAt in dry DMF (1-2 mL) and 4 eq of DIPEA in dry DMF (1-2 mL) were added to the peptide, followed by stirring for ca. 16 h. The volatiles were removed by evaporation. The crude cyclic peptide was dissolved in 7 mL of $CH_2Cl_2$ and washed three times with 4.5 mL 10% acetonitrile in water (v/v). The $CH_2Cl_2$ layer was then evaporated to dryness.

To fully deprotect the peptide, 7 mL of cleavage cocktail TFA/DODT/thioanisol/$H_2O$ (87.5:2.5:5:5) or TFA/TIS/$H_2O$ (95:2.5:2.5) were added, and the mixture was kept for 2.5-4 h at room temperature until the reaction was completed. The reaction mixture was evaporated close to dryness, the peptide precipitated with 7 mL of cold Et$_2$O/pentane and finally washed 3 times with 4 mL of cold Et$_2$O/pentane.

Procedure B: Cyclization and Work Up of a Backbone Cyclized Peptide Having a Disulfide Interstrand Linkage Formation of a Disulfide Interstrand Linkage After cleavage, backbone cyclization and deprotection of the linear peptide, as described in the corresponding section of procedure A, the deprotected cyclic peptide was treated with 0.5 mL of DMSO in a solution of 9.5 mL H$_2$O/AcOH (95:5; adjusted to pH=6 with NH$_4$HCO$_3$) for 24 h at rt to form the disulfide bridge. Thereafter, the reaction mixture was evaporated to dryness.

Procedure C: Cyclization and Work Up of a Backbone Cyclized Peptide Having a Lactam Interstrand Linkage Formation of a Lactam Interstrand Linkage Following assembly of the linear peptide, the resin was swelled in 5 mL of freshly distilled CH$_2$Cl$_2$ for at least 15 min. To selectively remove alloc- and allyl-protecting groups from amino and carboxyl functions, respectively, 0.2 eq tetrakis(triphenyl-phosphine)palladium(0) (10 mM) in dry CH$_2$Cl$_2$ and 10 eq phenylsilane were added. After shaking the reaction mixture for 15 min at rt, the resin was filtered off and a fresh solution of reagents was added to repeat the procedure. Following subsequent washing of the resin with CH$_2$Cl$_2$, DMF and Et$_2$O the resin was swelled in 5 mL DMF. 1 mL of a DIPEA solution in DMF (24.6 μl DIPEA in 1 mL DMF, 4 eq) was added followed by a 1 mL HATU solution in DMF (27.4 mg HATU in DMF, 2 eq). After stirring the reaction mixture overnight the resin was filtered and washed thoroughly with DMF and CH$_2$Cl$_2$.

Cleavage, backbone cyclization and deprotection of the modified peptide was performed as described in the corresponding sections of procedure A.

Procedure D: Cyclization and Work Up of a Backbone Cyclized Peptide Having an Urea Interstrand Linkage Formation of an Urea Interstrand Linkage Following cleavage and backbone cyclization as described in the corresponding sections of procedure A, the fully protected peptide was dissolved in 10 mL CH$_2$Cl$_2$ and 0.2 mL phenylsilane (30 eq) as well as a solution of tetrakis(triphenylphosphine)-palladium(0) (0.2 eq) in 1 mL CH$_2$Cl$_2$ were added. The mixture was stirred 45 min at rt to complete the removal of the alloc protecting groups. After evaporation to a final volume of 2 mL, the peptide was precipitated with 40 mL of cold Et$_2$O/pentane. The precipitate was washed 3 times with cold Et$_2$O/pentane and the air-dried solid was dissolved in 30 mL dry CH$_2$Cl$_2$. After addition of 6 eq DIPEA, di(N-succinimidyl)carbonate (1.2 eq) dissolved in 10 mL dry CH$_2$Cl$_2$ was added dropwise within 25 min to the reaction mixture. Following 1 h stirring at rt, 10 μl ethylenediamine (2.5 eq) and 10 mL H$_2$O were added subsequently to quench the excess of di(N-succinimidyl)carbonate. After discarding the aqueous phase the organic phase was evaporated to dryness and the modified peptide was deprotected as described in the corresponding section of procedure A.

Purification Procedure (Preparative Reverse Phase LC-MS)

Compounds were purified by reverse phase chromatography using a Phenomenex Gemini NX-C18 column, 30×100 mm, 5 μm (Cat No. 00D-4435-U0-AX) or a Waters XBridge C18 OBD column, 30×100 mm, 5 μm (Cat No. 186002982).

Mobile phases used were:
A: 0.1% TFA in Water/Acetonitrile 95/5 v/v
B: 0.1% TFA in Acetonitrile Gradient slopes in the preparative runs were adapted each time based on analytical LC-MS analysis of the crude product. As an example, a typical run was executed using the Phenomenex column with a flow rate of 35 mL/min running a gradient from 0-1 min 0% B, at 1.1 min 25% B to a final of 8 min 45% B (retention time: 5.96 min in this case).

Detection: MS and UV @ 220 nm

Fractions collected were evaporated using a Genevac HT4 evaporator or a Büchi system.

Alternatively for larger amounts the following LC-purification system was used:

Column: Waters XBridge C18 OBD column, 50×250 mm, 10 μm (Cat No. 186003900)
Mobile phase A: 0.1% TFA in Water
Mobile phase B: Acetonitrile
Flow rate: 150 mL/min
Detection: UV @ 220 nm After lyophilisation the products were obtained typically as white to off-white powders and analysed by HPLC-ESI-MS methods as described below. Analytical data after preparative HPLC purification are shown in Table 1.

1.2 Analytical Methods

Analytical Method A:

Analytical HPLC retention times (RT, in minutes) were determined using Ascentis Express C8 column, 100×3 mm, 2.7 μm, with the following solvents A (H$_2$O+0.1% TFA) and B(CH$_3$CN+0.085% TFA) and the gradient: 0-0.1 min: 95% A, 5% B; 11 min: 15% A, 85% B; 11.02-12.5 min: 3% A, 97% B; 12.55-13.5 min: 95% A, 5% B. Flow rate 1.3 mL/min at 55° C.

Analytical Method B:

Analytical HPLC retention times (RT, in minutes) were determined using Ascentis Express C8 column, 100×3 mm, 2.7 μm, with the following solvents A (H$_2$O+0.1% TFA) and B(CH$_3$CN+0.085% TFA) and the gradient: 0-0.1 min: 95% A, 5% B; 7 min: 15% A, 85% B; 7.02 min: 3% A, 97% B; 7.02-7.5 min: 3% A, 97% B; 7.52-7.75 min: 95% A, 5% B. Flow rate 1.4 mL/min at 55° C.

Analytical Method C:

Analytical HPLC retention times (RT, in minutes) were determined using Ascentis Express C8 column, 100×3 mm, 2.7 μm, with the following solvents A (H$_2$O+0.1% TFA) and B(CH$_3$CN+0.085% TFA) and the gradient: 0-0.1 min: 95% A, 5% B; 7 min: 45% A, 55% B; 7.02 min: 3% A, 97% B; 7.02-7.5 min: 3% A, 97% B; 7.52-7.75 min: 95% A, 5% B. Flow rate 1.4 mL/min at 55° C.

Analytical Method D:

Analytical HPLC retention times (RT, in minutes) were determined using Ascentis Express C18 column, 50×3 mm, 2.7 μm, with the following solvents A (H$_2$O+0.1% TFA) and B(CH$_3$CN+0.085% TFA) and the gradient: 0-0.05 min: 97% A, 3% B; 3.4 min: 45% A, 55% B; 3.45 min-3.65 min: 3% A, 97% B; 3.67 min-3.7 min: 97% A, 3% B. Flow rate 1.3 mL/min at 55° C.

Analytical Method E:

Analytical HPLC retention times (RT, in minutes) were determined using Ascentis Express C18 column, 50×2.1 mm, 2.7 μm, with the following solvents A (H$_2$O+0.1% TFA and B(CH$_3$CN+0.085% TFA) and the gradient: 0-0.05 min: 97% A, 3% B; 3.3 min: 15% A, 85% B; 3.32 min: 3% A, 97% B; 3.32-3.55 min: 3% A, 97% B; 3.57-3.7 min: 97% A, 3% B. Flow rate 1.6 mL/min at 55° C.

1.3 Synthesis of Peptide Sequences

Example 1 is shown in Table 1.

The peptide was synthesized according the general method starting with the amino acid (S)-2-amino-4-(tert-butoxycarbonylamino)butanoic acid, which was grafted to the resin (Fmoc-Dab(Boc)-2-chlorotrityl resin). The linear peptide was synthesized on the solid support according to the procedure described above in the following sequence: Resin-Dab-$P^5$-$P^4$-$P^3$-$P^2$-$P^1$-$T^2$-$T^1$-$P^{12}$-$P^{11}$-$P^{10}$-$P^9$-$P^8$-$P^7$. After cleavage from resin, backbone cyclization and deprotection, the disulfide β-strand linkage was formed as indicated in procedure B. Finally, the peptides was purified by preparative reverse phase LC-MS, as described above. After lyophilisation the products was obtained as white to off-white powders and characterised by HPLC-MS. For analytical data, see Ex. 1 in Table 1.

Examples 2-6 are shown in Table 1.

The peptides were synthesized according the general method starting with the amino acid (R)-2-amino-4-(tert-butoxycarbonylamino)butanoic acid, which was grafted to the resin (Fmoc-$^D$Dab(Boc)-2-chlorotrityl resin). The linear peptides were synthesized on the solid support according to the procedure described above in the following sequence: Resin-$^D$Dab-$P^5$-$P^4$-$P^3$-$P^2$-$P^1$-$T^2$-$T^1$-$P^{12}$-$P^{11}$-$P^{10}$-$P^9$-$P^8$-$P^7$. After cleavage from resin, backbone cyclization and deprotection, the disulfide β-strand linkages were formed as indicated in procedure B. Finally, the peptides were purified by preparative reverse phase LC-MS, as described above. After lyophilisation the products were obtained as white to off-white powders and characterised by HPLC-MS. For analytical data, see Ex. 2-6 in Table 1.

Examples 7-9 are shown in Table 1.

The peptides were synthesized according the general method starting with the amino acid (S)-2-amino-4-(tert-butoxycarbonylamino)butanoic acid, which was grafted to the resin (Fmoc-Dab(Boc)-2-chlorotrityl resin). The linear peptides were synthesized on the solid support according to the procedure described above in the following sequence: Resin-Dab-$P^6$-$P^5$-$P^4$-$P^3$-$P^2$-$P^1$-$T^2$-$T^1$-$P^{12}$-$P^{11}$-$P^{10}$-$P^9$-$P^8$. After cleavage from resin, backbone cyclization and deprotection, the disulfide β-strand linkages were formed as indicated in procedure B. Finally, the peptides were purified by preparative reverse phase LC-MS, as described above. After lyophilisation the products were obtained as white to off-white powders and characterised by HPLC-MS. For analytical data, see Ex. 7-9 in Table 1.

Examples 10, 11 are shown in Table 1.

The peptides were synthesized according the general method starting with the amino acid Fmoc-Trp(Boc)-OH, which was grafted to the resin (Fmoc-Trp(Boc)-2-chlorotrityl resin). The linear peptides were synthesized on the solid support according to the procedure described above in the following sequence: Resin-Trp-$P^7$-$P^6$-$P^5$-$P^4$-$P^3$-$P^1$-$T^2$-$T^1$-$P^{12}$-$P^{11}$-$P^{10}$-$P^9$. After cleavage from resin, backbone cyclization and deprotection, the disulfide β-strand linkages were formed as indicated in procedure B. Finally, the peptides were purified by preparative reverse phase LC-MS, as described above. After lyophilisation the products were obtained as white to off-white powders and characterised by HPLC-MS. For analytical data, see Ex. 10, 11 Table 1.

Examples 38, 39 are shown in Table 1.

The peptides were synthesized according the general method starting with the amino acid L-proline, which was grafted to the resin (Fmoc-Pro-2-chlorotrityl resin). The linear peptides were synthesized on the solid support according to the procedure described above in the following sequence: Resin-Pro-$T^1$-$P^{12}$-$P^{11}$-$P^{10}$-$P^9$-$P^8$-$P^7$-$P^6$-$P^5$-$P^4$-$P^3$-$P^2$-$P^1$. After cleavage from resin, backbone cyclization and deprotection, the disulfide β-strand linkages were formed as indicated in procedure B. Finally, the peptides were purified by preparative reverse phase LC-MS, as described above. After lyophilisation the products was obtained as white to off-white powders and characterised by HPLC-MS. For analytical data, see Ex. 38, 39 in Table 1.

Examples 12-33 are shown in Table 1.

The peptides were synthesized according the general method starting with the amino acid (S)-2-amino-4-(tert-butoxycarbonylamino)butanoic acid, which was grafted to the resin (Fmoc-Dab(Boc)-2-chlorotrityl resin). The linear peptides were synthesized on the solid support according to the procedure described above in the following sequence: Resin-Dab-$P^6$-$P^5$-$P^4$-$P^3$-$P^2$-$P^1$-$T^2$-$T^1$-$P^{12}$-$P^{11}$-$P^{10}$-$P^9$-$P^8$.
Then the lactam β-strand linkages were formed as indicated in procedure C. After cleavage from resin, backbone cyclization and deprotection, the peptides were purified by preparative reverse phase LC-MS, as described above. After lyophilisation the products were obtained as white to off-white powders and characterised by HPLC-MS. For analytical data, see Ex. 12-33 in Table 1.

Examples 34-37 are shown in Table 1.

The peptides were synthesized according the general method starting with the amino acid L-proline, which was grafted to the resin (Fmoc-Pro-2-chlorotrityl resin). The linear peptides were synthesized on the solid support according to the procedure described above in the following sequence: Resin-Pro-$T^1$-$P^{12}$-$P^{11}$-$P^{10}$-$P^9$-$P^8$-$P^7$-$P^6$-$P^4$-$P^3$-$P^2$-$P^1$. Then, the lactam β-strand linkages were formed as indicated in procedure C. After cleavage from resin, backbone cyclization and deprotection, the peptides were purified by preparative reverse phase LC-MS, as described above. After lyophilisation the products were obtained as white to off-white powders and characterised by HPLC-MS. For analytical data, see Ex. 34-37 in Table 1.

Example 40 is shown in Table 1.

The peptide was synthesized according the general method starting with the amino acid L-proline, which was grafted to the resin (Fmoc-Pro-2-chlorotrityl resin). The linear peptide was synthesized on the solid support according to the procedure described above in the following sequence: Resin-Pro-$T^1$-$P^{12}$-$P^{11}$-$P^{10}$-$P^9$-$P^8$-$P^7$-$P^6$-$P^5$-$P^4$-$P^3$-$P^2$-$P^1$. Following cleavage and backbone cyclization, the urea β-strand linkage was formed as indicated in procedure D. Following deprotection, the peptide was purified by preparative reverse phase LC-MS, as described above. After lyophilisation the product was obtained as white to off-white powders and characterised by HPLC-MS. For analytical data, see Ex. 40 in Table 1.

Example 41 is shown in Table 1.

The peptides was synthesized according the general method starting with the amino acid (S)-2-amino-4-(tert-butoxycarbonylamino)butanoic acid, which was grafted to the resin (Fmoc-Dab(Boc)-2-chlorotrityl resin). The linear peptide were synthesized on the solid support according to the procedure described above in the following sequence: Resin-Dab-$P^6$-$P^5$-$P^4$-$P^3$-$P^2$-$P^1$-$T^2$-$T^1$-$P^{12}$-$P^{11}$-$P^{10}$-$P^9$-$P^8$. After cleavage from resin, backbone cyclization and deprotection, as indicated in procedure A, the peptide was purified by preparative reverse phase LC-MS, as described above. After lyophilisation the product was obtained as white to off-white powders and characterised by HPLC-MS. For analytical data, see Ex. 41 in Table 1.

Examples 42-44 are shown in Table 1.

The peptides were synthesized according the general method starting with the amino acid Fmoc-Trp(Boc)-OH, which was grafted to the resin (Fmoc-Trp(Boc)-2-chlorotrityl resin). The linear peptides were synthesized on the solid support according to the procedure described above in the following sequence: Resin-Trp-$P^7$-$P^6$-$P^5$-$P^4$-$P^3$-$P^2$-$P^1$-$T^2$-$T^1$-$P^{12}$-$P^{11}$-$P^{10}$-$P^9$. After cleavage from resin, backbone cyclization and deprotection, as indicated in procedure A, the peptides were purified by preparative reverse phase LC-MS, as described above. After lyophilisation the products were obtained as white to off-white powders and characterised by HPLC-MS. For analytical data, see Ex. 42-44 in Table 1.

1.4 Sequence Data

National Committee for Clinical laboratory standards, Wayne, Pa.) with slight modifications. Inocula of the microorganisms were diluted into Mueller-Hinton II (MH, cation adjusted) broth and compared with a 0.5 McFarland standard to give appr. $10^6$ colony forming units (CFU)/mL. Aliquots (90 µl) of inoculate were added to 10 µl of MH broth+P-80 (Polysorbate 80, 0.002% final concentration)

TABLE 1

Examples (Ex.)

| Ex.[c] | P1 [a] | P2 [a] | P3 [a] | P4 [a] | P5 [a] | P6 [a] | P7 [a] | P8 [a] | P9 [a] | P10 [a] | P11 [a] | P12 [a] | T1 [a] | T2 [a] | Analyt. Meth. | MS [b] | RT [min] | Purity [%] |
|---|---|---|---|---|---|---|---|---|---|---|---|---|---|---|---|---|---|---|
| 1 | Leu | Cys | Tyr | Ala | Dab | Dab | Dab | Trp | Ala | Val | Cys | Val | DPro | Dab | D | 752.8 | 1.94 | 93 |
| 2 | Leu | Cys | Tyr | Ala | Dab | DDab | Dab | Trp | Ala | Val | Cys | Val | DPro | Dab | D | 753.3 | 2.00 | 91 |
| 3 | Leu | Cys | Tyr | Ala | Orn | DDab | Dab | Trp | Ala | Val | Cys | Val | DPro | Lys | D | 773.8 | 2.01 | 87 |
| 4 | Leu | Cys | Tyr | Ala | Orn | DDab | Dab | Trp | Ala | Val | Cys | Val | DPro | Orn | D | 767.3 | 1.98 | 87 |
| 5 | Leu | Cys | Tyr | Ala | Orn | DDab | Dab | Trp | Ala | Val | Cys | Val | DPro | Dab | D | 759.8 | 1.98 | 91 |
| 6 | Leu | Cys | Tyr | Ala | Orn | DDab | Dab | Trp | Ala | Val | Cys | Val | DPro | Dap | D | 752.8 | 1.98 | 91 |
| 7 | Ile | Cys | Tyr | Dab | Orn | DDab | Dab | Leu | Dab | Val | Cys | Tyr | DPro | Pro | B | 783.4 | 2.72 | 89 |
| 8 | Val | Cys | Tyr | Dab | Dap | Dab | Dab | Trp | Dab | tBuGly | Cys | Thr | DPro | Pro | B | 774.4 | 2.58 | 95 |
| 9 | Val | Cys | Tyr | Dab | Dap | DDab | Dab | Trp | Dab | tBuGly | Cys | Ser | DPro | NMeAla | B | 761.4 | 2.43 | 87 |
| 10 | Ile | Cys | Tyr | Dab | Orn | DDab | Dab | Trp | Dab | tBuGly | Cys | Ser | DPro | Pro | E | 788.7 | 1.18 | 88 |
| 11 | Ile | Cys | Tyr | Dab | Orn | DDab | Dab | Trp | Dab | tBuGly | Cys | Ser | DPro | Tyr | B | 821.8 | 2.43 | 90 |
| 12 | Val | Dab | Tyr | Dab | Dap | DDab | Dab | Trp | Dab | tBuGly | Asp | Thr | DAzt | Pro | B | 763.9 | 2.60 | 93 |
| 13 | Phe | Dab | Tyr | Arg | Orn | DDab | Dab | Trp | Dab | tBuGly | Asp | Ser | DPro | Pro | B | 830.4 | 2.69 | 94 |
| 14 | Trp | Dab | Tyr | Dab | Dab | DDab | Dab | Trp | Dab | tBuGly | Asp | Ser | DPro | Pro | C | 814.4 | 3.75 | 90 |
| 15 | Trp | Dab | Tyr | Dab | Dab | Dab | Dab | Trp | Dab | tBuGly | Asp | Ser | DAzt | Pro | B | 807.4 | 2.47 | 94 |
| 16 | Val | Dab | Tyr | Dab | Dab | DDab | Dab | Trp | Dab | Phg | Asp | Ser | DPro | Pro | B | 780.9 | 2.48 | 91 |
| 17 | Val | Dab | Tyr | Dab | Thr | Dab | Dab | Trp | Dab | tBuGly | Asp | His | DPro | Pro | B | 796.4 | 2.18 | 95 |
| 18 | Leu | Glu | Tyr | Dab | Orn | Dab | Dab | Trp | Dab | tBuGly | Dap | Ser | DPro | Pro | A | 785.3 | 4.25 | 91 |
| 19 | Leu | Glu | Tyr | Dab | Orn | DDab | Dab | Trp | Dab | tBuGly | Dab | Ser | DPro | Pro | A | 792.3 | 4.16 | 88 |
| 20 | Leu | Glu | Tyr | Dab | Orn | DDab | Dab | Trp | Dab | tBuGly | Lys | Ser | DPro | Pro | A | 806.3 | 4.14 | 87 |
| 21 | Leu | Asp | Tyr | Dab | Orn | DDab | Dab | Trp | Dab | tBuGly | Dap | Ser | DPro | Pro | A | 778.2 | 4.27 | 92 |
| 22 | Leu | Asp | Tyr | Dab | Orn | DDab | Dab | Trp | Dab | tBuGly | Dab | Ser | DPro | Pro | A | 785.0 | 4.34 | 92 |
| 23 | Leu | Asp | Tyr | Dab | Orn | Dab | Dab | Trp | Dab | tBuGly | Dab | Ser | DPro | Pro | A | 785.2 | 4.21 | 89 |
| 24 | Leu | Asp | Tyr | Dab | Orn | DDab | Dab | Trp | Dab | tBuGly | Lys | Ser | DPro | Pro | A | 799.4 | 4.35 | 81 |
| 25 | Leu | Asp | Tyr | Dab | Orn | Dab | Dab | Trp | Dab | tBuGly | Lys | Ser | DPro | Pro | A | 799.3 | 4.26 | 88 |
| 26 | Leu | Dap | Tyr | Dab | Orn | Dab | Dab | Trp | Dab | tBuGly | Glu | Ser | DPro | Pro | A | 758.2 | 4.18 | 93 |
| 27 | Leu | Lys | Tyr | Dab | Orn | DDab | Dab | Trp | Dab | tBuGly | Glu | Ser | DPro | Pro | A | 806.4 | 4.38 | 76 |
| 28 | Val | Dab | Tyr | Dab | Dab | DDab | Dab | Trp | Dab | tBuGly | Asp | Ser | DPro | Pro | B | 770.9 | 2.45 | 88 |
| 29 | Leu | Dap | Tyr | Dab | Orn | DDab | Dab | Trp | Dab | tBuGly | Glu | Ser | DPro | Pro | A | 785.4 | 4.33 | 83 |
| 30 | Leu | Dab | Tyr | Dab | Orn | DDab | Dab | Trp | Dab | tBuGly | Glu | Ser | DPro | Pro | A | 792.2 | 4.31 | 77 |
| 31 | Leu | Dap | Tyr | Dab | Orn | Dab | Dab | Trp | Dab | tBuGly | Asp | Ser | DPro | Pro | A | 778.0 | 4.11 | 95 |
| 32 | Leu | Dab | Tyr | Dab | Orn | Dab | Dab | Trp | Dab | tBuGly | Asp | Ser | DPro | Pro | A | 785.0 | 4.33 | 89 |
| 33 | Leu | Lys | Tyr | Dab | Orn | Dab | Dab | Trp | Dab | tBuGly | Asp | Ser | DPro | Pro | A | 799.3 | 4.44 | 81 |
| 34 | Leu | Glu | Tyr | Dab | Orn | DDab | Dab | Trp | Dab | tBuGly | Dap | Ser | DPro | Pro | A | 785.2 | 4.35 | 80 |
| 35 | Leu | Lys | Tyr | Dab | Orn | DDab | Dab | Trp | Dab | tBuGly | Asp | Ser | DPro | Pro | A | 799.2 | 4.41 | 91 |
| 36 | Leu | Dap | Tyr | Dab | Orn | DDab | Dab | Trp | Dab | tBuGly | Asp | Ser | DPro | Pro | A | 778.2 | 4.54 | 95 |
| 37 | Leu | Dab | Tyr | Dab | Orn | DDab | Dab | Trp | Dab | tBuGly | Asp | Ser | DPro | Pro | A | 785.2 | 4.38 | 83 |
| 38 | Val | DCys | Tyr | Dab | Dap | DDab | Dab | Trp | Dab | tBuGly | DCys | Ser | DPro | Pro | B | 767.4 | 3.01 | 87 |
| 39 | Val | Hcy | Tyr | Dab | Dap | DDab | Dab | Trp | Dab | tBuGly | Cys | Ser | DPro | Pro | B | 774.4 | 2.45 | 90 |
| 40 | Val | Dap | Tyr | Dab | Dap | DDab | Dab | Trp | Dab | tBuGly | Dap | Ser | DPro | Pro | A | 764.4 | 3.42 | 77 |
| 41 | Val | Dap | Tyr | Dab | Dap | DDab | Dab | Trp | Dab | tBuGly | Ser | Thr | DAzt | Pro | B | 751.9 | 2.45 | 95 |
| 42 | Phe | Dap | Tyr | Dab | Orn | DDab | Dab | Trp | Dab | tBuGly | Ala | Ser | DPro | Leu | B | 790.2 | 2.63 | 91 |
| 43 | Phe | Dap | Tyr | Dab | Orn | DDab | Dab | Trp | Dab | tBuGly | Ala | Ser | DPro | Phe | B | 807.2 | 2.69 | 92 |
| 44 | Phe | Dap | Tyr | Dab | Orn | DDab | Dab | Trp | Dab | tBuGly | Ala | Ser | DPro | Tyr | B | 815.2 | 2.42 | 89 |

[a] Abbreviations of amino acid see listing above.
[b] MS: either $[M + 2H]^{2+}$ or $[M + 3H]^{3+}$.
[c] The sequences of Examples 1-11, 38, 39 have disulfide linkages between P2 and P11, as described above, the sequences of Examples 12-37 have lactam linkages between P2 and P11, as described above, and the sequence of Example 40 has an urea linkage between P2 and P11, as described above.

2. Biological Methods 2.1. Preparation of the Peptides

Lyophilized peptides were weighed on a Microbalance (Mettler MT5) and dissolved in sterile water to a final concentration of 1 mg/mL. Stock solutions were kept at +4° C., light protected.

2.2. Antimicrobial Activity of the Peptides

The selective antimicrobial activities of the peptides were determined in 96-well plates (Greiner, polystyrene) by the standard NCCLS broth microdilution method (National Committee for Clinical Laboratory Standards 1993. Methods for dilution antimicrobial susceptibility tests for bacteria that grow aerobically, 3rd ed. Approved standard M7-A6; containing the peptide in serial two-fold dilutions. The following microorganisms were used to determine antibiotic selectivity of the peptides: *Escherichia coli* ATCC 25922, *Klebsiella pneumoniae* ATCC 13883 and *Acinetobacter baumannii* DSM 30008. Antimicrobial activities of the peptides were expressed as the minimal inhibitory concentration (MIC) in µg/mL at which no visible growth was observed after 18-20 hours of incubation at 35° C.

2.3. Hemolysis

The peptides were tested for their hemolytic activity against human red blood cells (hRBC). Fresh hRBC were washed three times with phosphate buffered saline (PBS) and centrifuged for 5 min at 3000×g. Compounds (100

μg/mL) were incubated with 20% hRBC (v/v) for 1 h at 37° C. and shaking at 300 rpm. The final erythrocyte concentration was approximately $0.9 \times 10^9$ cells/mL. A value of 0% and 100% cell lyses, respectively, was determined by incubation of hRBC in the presence of PBS containing 0.001% acetic acid and 2.5% Triton X-100 in $H_2O$, respectively. The samples were centrifuged, the supernatants were 8-fold diluted in PBS buffer and the optical densities (OD) were measured at 540 nm. The 100% lyses value ($OD_{540}H_2O$) gave an $OD_{540}$ of approximately 0.5-1.0.

Percent hemolysis was calculated as follows: ($OD_{540}$peptide/$OD_{540}H_2O$)×100%.

The results of the experiments described in 2.2-2.3 are indicated in Table 2 herein below.

TABLE 2

Minimal inhibitory concentrations (MIC) in Mueller-Hinton broth II, and hemolysis

| Ex. | Escherichia coli ATCC 25922 MIC [μg/mL] | Klebsiella pneumoniae ATCC 13883 MIC [μg/mL] | Acinetobacter baumannii DSM 30008 MIC [μg/mL] | Hemolysis at 100 μg/mL [%] |
|---|---|---|---|---|
| 1 | 4 | 2 | 2.5 | 2 |
| 2 | 2 | 2 | 2.5 | 3 |
| 3 | 2 | 4 | 1 | 3.5 |
| 4 | 2 | 4 | 2 | 2.5 |
| 5 | 2 | 2 | 1 | 3 |
| 6 | 2 | 2 | 1.5 | 5 |
| 7 | 0.5 | 0.25 | 1 | 11 |
| 8 | 1 | 0.5 | 2 | 1 |
| 9 | 0.5 | 1 | 1 | 6 |
| 10 | 1 | 0.25 | 1 | 1 |
| 11 | 2 | 0.5 | 1 | 1 |
| 12 | 0.5 | 0.25 | 1 | 4 |
| 13 | 0.25 | 0.5 | 1 | 1 |
| 14 | 0.25 | 0.25 | 0.5 | 2 |
| 15 | 0.25 | 0.25 | 0.5 | 1 |
| 16 | 0.5 | 0.5 | 1 | 1 |
| 17 | 2 | 2 | 4 | 1 |
| 18 | 2 | 0.5 | 3 | 0 |
| 19 | 3 | 8 | 3 | 0 |
| 20 | 2 | 1 | 4 | 0 |
| 21 | 2 | 0.5 | 4 | 1 |
| 22 | 0.5 | 0.5 | 1 | 1.5 |
| 23 | 1 | 0.5 | 1 | 0 |
| 24 | 0.5 | 0.5 | 1 | 0.5 |
| 25 | 1 | 1 | 2 | 0 |
| 26 | 4 | 1 | 4 | 0 |
| 27 | 4 | 2 | 3 | 0.5 |
| 28 | 0.5 | 0.5 | 2 | 1 |
| 29 | 1 | 0.5 | 1 | 0.5 |
| 30 | 1 | 2 | 1 | 0.5 |
| 31 | 2 | 2 | 4 | 0 |
| 32 | 0.5 | 0.5 | 0.5 | 1 |
| 33 | 1 | 4 | 1 | 1 |
| 34 | 0.5 | 0.5 | 1 | 1 |
| 35 | 0.5 | 2 | 1 | 0 |
| 36 | 0.5 | 0.125 | 1.5 | 4.5 |
| 37 | 0.5 | 0.5 | 0.5 | 2.5 |
| 38 | 4 | 2 | 2 | 2 |
| 39 | 1 | 1 | 2 | 2 |
| 40 | 0.25 | 0.25 | 1 | 2 |
| 41 | 0.5 | 0.25 | 1 | 1 |
| 42 | 1 | 1 | 4 | 1 |
| 43 | 1 | 0.25 | 1 | 1 |
| 44 | 0.5 | 0.25 | 1 | 0 |

The invention claimed is:

1. A compound of the general formula (I), cyclo[$P^1$-$P^2$-$P^3$-$P^4$-$P^5$-$P^6$-$P^7$-$P^8$-$P^9$-$P^{10}$-$P^{11}$-$P^{12}$-$T^1$-$T^2$]  (I)

wherein the single elements T or P are connected in either direction from the carbonyl (C=O) point of attachment to the nitrogen (N) of the next element and wherein $T^1$ is $^D$Pro; or $^D$Azt;
$T^2$ is Pro; Leu; NMeAla; Tyr; Phe; Dab; Dap; Orn; or Lys;
$P^1$ is Leu; Ile; Val; Phe; or Trp;
$P^2$ is Dab; Dap; or Lys;
$P^3$ is Tyr;
$P^4$ is Ala; Dab; or Arg;
$P^5$ is Orn; Dap; Dab; or Thr;
$P^6$ is Dab; or $^D$Dab;
$P^7$ is Dab;
$P^8$ is Trp; or Leu;
$P^9$ is Ala; or Dab;
$P^{10}$ is Val; tBuGly; or Phg;
$P^{11}$ is Ala; Ser; Asp; Glu; Dap; Dab, or Lys;
$P^{12}$ is Val; Tyr; His; Ser; or Thr;
$P^2$ and $P^{11}$ taken together and/or $P^4$ and $P^9$ taken together can form interstrand linking bis(amino acid)-structures based on the linkage of two L- or D-amino acid residues following connection of the side chain of Cys; or Hcy; with the side chain of Cys; or Hcy; by a disulfide linkage; or
connection of the side chain of Dap; Dab; or Lys; with the side chain of Asp; or Glu; by a lactam linkage; or
connection of the side chain of Dap; with the side chain of Dap; by an urea linkage;
or a pharmaceutically acceptable salt thereof;
or a tautomer or rotamer thereof, or a salt, or a hydrate or solvate thereof;
with the proviso that
if no interstrand linkage is formed;
and
$T^1$ is $^D$Pro;
then
$T^2$ is Leu; NMeAla; Tyr; Phe; Dab; Dap; Orn; or Lys.

2. The compound according to claim 1 which is selected from a group consisting of β-hairpin peptidomimetics of general formula (I) having a disulfide linkage; a lactam linkage; or a urea linkage between $P^2$ and $P^{11}$:

cyclo(-Leu-Cys-Tyr-Ala-Dab-Dab-Dab-Trp-Ala-Val-Cys-Val-$^D$Pro-Dab-);
cyclo(-Leu-Cys-Tyr-Ala-Dab-$^D$Dab-Dab-Trp-Ala-Val-Cys-Val-$^D$Pro-Dab-);
cyclo(-Leu-Cys-Tyr-Ala-Orn-$^D$Dab-Dab-Trp-Ala-Val-Cys-Val-$^D$Pro-Lys-);
cyclo(-Leu-Cys-Tyr-Ala-Orn-$^D$Dab-Dab-Trp-Ala-Val-Cys-Val-$^D$Pro-Orn-);
cyclo(-Leu-Cys-Tyr-Ala-Orn-$^D$Dab-Dab-Trp-Ala-Val-Cys-Val-$^D$Pro-Dab-);
cyclo(-Leu-Cys-Tyr-Ala-Orn-$^D$Dab-Dab-Trp-Ala-Val-Cys-Val-$^D$Pro-Dap-);
cyclo(-Ile-Cys-Tyr-Dab-Orn-$^D$Dab-Dab-Leu-Dab-Val-Cys-Tyr-$^D$Pro-Pro-);
cyclo(-Val-Cys-Tyr-Dab-Dap-Dab-Dab-Trp-Dab-tBu-Gly-Cys-Thr-$^D$Pro-Pro-);
cyclo(-Val-Cys-Tyr-Dab-Dap-$^D$Dab-Dab-Trp-Dab-tBu-Gly-Cys-Ser-$^D$Pro-NMeAla-);
cyclo(-Ile-Cys-Tyr-Dab-Orn-$^D$Dab-Dab-Trp-Dab-tBu-Gly-Cys-Ser-$^D$Pro-Pro-);
cyclo(-Ile-Cys-Tyr-Dab-Orn-$^D$Dab-Dab-Trp-Dab-tBu-Gly-Cys-Ser-$^D$Pro-Tyr-);
cyclo(-Val-Dab-Tyr-Dab-Dap-$^D$Dab-Dab-Trp-Dab-tBu-Gly-Asp-Thr-$^D$Azt-Pro-);
cyclo(-Phe-Dab-Tyr-Arg-Orn-$^D$Dab-Dab-Trp-Dab-tBu-Gly-Asp-Ser-$^D$Pro-Pro-);
cyclo(-Trp-Dab-Tyr-Dab-Dab-$^D$Dab-Dab-Trp-Dab-tBu-Gly-Asp-Ser-$^D$Pro-Pro-);
cyclo(-Trp-Dab-Tyr-Dab-Dab-Dab-Dab-Trp-Dab-tBu-Gly-Asp-Ser-$^D$Azt-Pro-);

cyclo(-Val-Dab-Tyr-Dab-Dab-$^D$Dab-Dab-Trp-Dab-Phg-Asp-Ser-$^D$Pro-Pro-);
cyclo(-Val-Dab-Tyr-Dab-Thr-Dab-Dab-Trp-Dab-tBuGly-Asp-His-$^D$Pro-Pro-);
cyclo(-Leu-Glu-Tyr-Dab-Orn-Dab-Dab-Trp-Dab-tBu-Gly-Dap-Ser-$^D$Pro-Pro-);
cyclo(-Leu-Glu-Tyr-Dab-Orn-$^D$Dab-Dab-Trp-Dab-tBu-Gly-Dab-Ser-$^D$Pro-Pro-);
cyclo(-Leu-Glu-Tyr-Dab-Orn-$^D$Dab-Dab-Trp-Dab-tBu-Gly-Lys-Ser-$^D$Pro-Pro-);
cyclo(-Leu-Asp-Tyr-Dab-Orn-$^D$Dab-Dab-Trp-Dab-tBu-Gly-Dap-Ser-$^D$Pro-Pro-);
cyclo(-Leu-Asp-Tyr-Dab-Orn-$^D$Dab-Dab-Trp-Dab-tBu-Gly-Dab-Ser-$^D$Pro-Pro-);
cyclo(-Leu-Asp-Tyr-Dab-Orn-Dab-Dab-Trp-Dab-tBu-Gly-Dab-Ser-$^D$Pro-Pro-);
cyclo(-Leu-Asp-Tyr-Dab-Orn-$^D$Dab-Dab-Trp-Dab-tBu-Gly-Lys-Ser-$^D$Pro-Pro-);
cyclo(-Leu-Asp-Tyr-Dab-Orn-Dab-Dab-Trp-Dab-tBu-Gly-Lys-Ser-$^D$Pro-Pro-);
cyclo(-Leu-Dap-Tyr-Dab-Orn-Dab-Dab-Trp-Dab-tBu-Gly-Glu-Ser-$^D$Pro-Pro-);
cyclo(-Leu-Lys-Tyr-Dab-Orn-$^D$Dab-Dab-Trp-Dab-tBu-Gly-Glu-Ser-$^D$Pro-Pro-);
cyclo(-Val-Dab-Tyr-Dab-Dab-$^D$Dab-Dab-Trp-Dab-tBu-Gly-Asp-Ser-$^D$Pro-Pro-);
cyclo(-Leu-Dap-Tyr-Dab-Orn-$^D$Dab-Dab-Trp-Dab-tBu-Gly-Glu-Ser-$^D$Pro-Pro-);
cyclo(-Leu-Dab-Tyr-Dab-Orn-Dab-Dab-Trp-Dab-tBu-Gly-Glu-Ser-$^D$Pro-Pro-);
cyclo(-Leu-Dap-Tyr-Dab-Orn-Dab-Dab-Trp-Dab-tBu-Gly-Asp-Ser-$^D$Pro-Pro-);
cyclo(-Leu-Dab-Tyr-Dab-Orn-Dab-Dab-Trp-Dab-tBu-Gly-Asp-Ser-$^D$Pro-Pro-);
cyclo(-Leu-Lys-Tyr-Dab-Orn-Dab-Dab-Trp-Dab-tBu-Gly-Asp-Ser-$^D$Pro-Pro-);
cyclo(-Leu-Glu-Tyr-Dab-Orn-$^D$Dab-Dab-Trp-Dab-tBu-Gly-Dap-Ser-$^D$Pro-Pro-);
cyclo(-Leu-Lys-Tyr-Dab-Orn-$^D$Dab-Dab-Trp-Dab-tBu-Gly-Asp-Ser-$^D$Pro-Pro-);
cyclo(-Leu-Dap-Tyr-Dab-Orn-$^D$Dab-Dab-Trp-Dab-tBu-Gly-Asp-Ser-$^D$Pro-Pro-);
cyclo(-Leu-Dab-Tyr-Dab-Orn-$^D$Dab-Dab-Trp-Dab-tBu-Gly-Asp-Ser-$^D$Pro-Pro-);
cyclo(-Val-$^D$Cys-Tyr-Dab-Dap-$^D$Dab-Dab-Trp-Dab-tBu-Gly-$^D$Cys-Ser-$^D$Pro-Pro-);
cyclo(-Val-Hcy-Tyr-Dab-Dap-$^D$Dab-Dab-Trp-Dab-tBu-Gly-Cys-Ser-$^D$Pro-Pro-);
cyclo(-Val-Dap-Tyr-Dab-Dap-$^D$Dab-Dab-Trp-Dab-tBu-Gly-Dap-Ser-$^D$Pro-Pro-);
or a pharmaceutically acceptable salt thereof;
and/or
a group consisting of β-hairpin peptidomimetics of general formula (I)
cyclo(-Val-Dap-Tyr-Dab-Dap-$^D$Dab-Dab-Trp-Dab-tBu-Gly-Se r-Thr-$^D$Azt-Pro-);
cyclo(-Phe-Dap-Tyr-Dab-Orn-$^D$Dab-Dab-Trp-Dab-tBu-Gly-Ala-Ser-$^D$Pro-Leu-);
cyclo(-Phe-Dap-Tyr-Dab-Orn-$^D$Dab-Dab-Trp-Dab-tBu-Gly-Ala-Ser-$^D$Pro-Phe-);
cyclo(-Phe-Dap-Tyr-Dab-Orn-$^D$Dab-Dab-Trp-Dab-tBu-Gly-Ala-Ser-$^D$Pro-Tyr-);
or a pharmaceutically acceptable salt thereof.

3. A diastereomer or epimer of the compound of formula (I) as defined in claim 1 based on one or more chiral center(s) not explicitly specified in formula (I) or an enantiomer of a compound of formula (I).

4. A pharmaceutical composition containing a compound or a mixture of compounds according to claim 1 and at least one pharmaceutically inert carrier.

5. The pharmaceutical composition according to claim 4 in a form suitable for oral, topical, transdermal, injection, buccal, transmucosal, rectal, pulmonary or inhalation administration, especially in the form of tablets, dragees, capsules, solutions, liquids, gels, plaster, creams, ointments, syrup, slurries, suspensions, spray, nebulizer or suppositories.

6. The compound of formula (I) according to claim 1, or a pharmaceutically acceptable salt thereof, for use as a medicament.

7. An antibiotic comprising the compound according to claim 1 as a pharmaceutically active substance.

8. A method of treating infections or diseases related to infections said diseases selected from respiratory diseases or skin or soft tissue diseases or gastrointestinal diseases or eye diseases or ear diseases or CNS diseases or bone diseases or cardiovascular diseases or genitourinary diseases comprising administering to a subject in need thereof the compound according to claim 1 or a composition containing the compound or a mixture of the compounds and at least one pharmaceutically inert carrier.

9. A process for the preparation of a compound according to claim 1 which comprises
a) coupling an appropriately functionalized solid support with an appropriately N-protected derivative of that amino acid which in the desired end-product is in position $T^1$ or $T^2$ or $P^1$ to $P^{12}$ as defined above; any functional group which may be present in said N-protected amino acid derivative being likewise appropriately protected;
(b) removing the N-protecting group from the product obtained in step (a);
(c) coupling the product thus obtained with an appropriately N-protected derivative of that amino acid which in the desired end-product is in the position of the next element (T or P), following counterclockwise or clockwise the sequence according to general formula (I) in —COOH to —NH2 orientation; any functional group which may be present in said N-protected amino acid derivative being likewise appropriately protected;
(d) removing the N-protecting group from the product thus obtained;
(e) repeating steps (c) and (d) until all amino acid residues have been introduced;
(f) if desired, selectively deprotecting one or several protected functional group(s) present in the molecule and chemically transforming the reactive group(s) thus liberated;
(g) detaching the product thus obtained from the solid support;
(h) cyclizing the product cleaved from the solid support;
(i) if desired, selectively deprotecting one or several protected functional group(s) present in the molecule and chemically transforming the reactive group(s) thus liberated;
(j) removing any protecting groups present on functional groups of any members of the chain of amino acid residues and, if desired, any protecting group(s) which may in addition be present in the molecule;
(k) if desired, implementing additional chemical transformations of one or more reactive group(s) present in the molecule; and
(l) if required, removing any protecting groups present on functional groups of any members of the chain of amino acid residues and, if desired, any protecting group(s) which may in addition be present in the molecule;

(m) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

10. A method of disinfecting or preserving foodstuffs, cosmetics, medicaments and other nutrient-containing materials, containing the step of adding the compound according to claim 1 to said foodstuffs, cosmetics, medicaments, and nutrient-containing materials.

11. A method of treating an infection selected from nosocomial infections, catheter-related and non-catheter-related infections, urinary tract infections, bloodstream infections, or a disease or disorder associated with an infection, selected from ventilator-associated pneumonia (VAP), hospital-acquired pneumonia (HAP), healthcare-associated pneumonia (HCAP), cystic fibrosis, emphysema, asthma, pneumonia, epidemic diarrhea, necrotizing enterocolitis, typhlitis, gastroenteritis, pancreatitis, keratitis, endophthalmitis, otitis, brain abscess, meningitis, encephalitis, osteochondritis, pericarditis, epididymitis, prostatitis, urethritis, surgical wounds, traumatic wounds, burns, comprising administering to a subject in need thereof a pharmaceutically acceptable amount of a compound according to claim 1 or a pharmaceutical composition containing the compound or a mixture of the compounds and at least one pharmaceutically inert carrier.

* * * * *